(12) United States Patent
Karbowicz et al.

(10) Patent No.: US 11,862,314 B2
(45) Date of Patent: Jan. 2, 2024

(54) METHODS AND SYSTEMS FOR PATIENT CONTROL OF AN ELECTRONIC PRESCRIPTION

(71) Applicant: Cambia Health Solutions, Inc., Portland, OR (US)

(72) Inventors: Sean Karbowicz, Portland, OR (US); Nicole Cathcart, Portland, OR (US); Mohan Nair, Lake Oswego, OR (US); Alex Thorpe, Beaverton, OR (US); Max Janasik, Portland, OR (US); Shawn Smith, Lake Oswego, OR (US); Diana Graalum, Portland, OR (US); Ronan Cranley, Portland, OR (US)

(73) Assignee: CAMBIA HEALTH SOLUTIONS, INC., Portland, OR (US)

( * ) Notice: Subject to any disclaimer, the term of this patent is extended or adjusted under 35 U.S.C. 154(b) by 567 days.

(21) Appl. No.: 16/669,357

(22) Filed: Oct. 30, 2019

(65) Prior Publication Data
US 2020/0135317 A1    Apr. 30, 2020

Related U.S. Application Data

(60) Provisional application No. 62/752,943, filed on Oct. 30, 2018.

(51) Int. Cl.
*G16H 20/10* (2018.01)
*G06Q 30/0201* (2023.01)
(Continued)

(52) U.S. Cl.
CPC ......... *G16H 20/10* (2018.01); *G06Q 30/0206* (2013.01); *G06Q 30/04* (2013.01); *G06Q 30/08* (2013.01); *G16H 10/60* (2018.01); *H04L 9/0637* (2013.01); *G06Q 20/3674* (2013.01); *G06Q 20/38215* (2013.01); *G06Q 20/40* (2013.01); *G06Q 30/02* (2013.01); *G06Q 30/06* (2013.01);
(Continued)

(58) Field of Classification Search
CPC .. G06F 16/182; G06F 21/606; G06F 21/6245; G06Q 20/36; G06Q 20/363; G06Q 30/04; G06Q 30/08; G16H 10/60; G16H 20/10; G16H 40/67; H04L 9/0637; H04L 2209/38; H04L 9/3236; H04L 9/3247
See application file for complete search history.

(56) References Cited

U.S. PATENT DOCUMENTS

2003/0018495 A1   1/2003  Sussman
2006/0229910 A1  10/2006  Longman et al.
(Continued)

FOREIGN PATENT DOCUMENTS

WO         0167345 A1      9/2001
WO   WO-2016079807 A1 *    5/2016  ............. G06Q 30/06

*Primary Examiner* — Jonathan Ng
*Assistant Examiner* — Hunter J Rasnic
(74) *Attorney, Agent, or Firm* — McCoy Russell LLP

(57) ABSTRACT

Methods and systems are provided for an online system for patient control of a medical prescription. In one example, a method is provided for transmitting a prescription to a first pharmacy in response to a patient selecting the first pharmacy for a first fill of the prescription. The method may further include transmitting the prescription to a second pharmacy in response to the patient selecting the second pharmacy, different than the first pharmacy, for a second fill of the prescription.

16 Claims, 11 Drawing Sheets

(51) Int. Cl.
*G06Q 30/08* (2012.01)
*H04L 9/06* (2006.01)
*G16H 10/60* (2018.01)
*G06Q 30/04* (2012.01)
*H04L 9/00* (2022.01)
*G16H 40/67* (2018.01)
*G16H 80/00* (2018.01)
*H04L 9/32* (2006.01)
*G06Q 20/40* (2012.01)
*G06Q 30/06* (2023.01)
*G06Q 20/38* (2012.01)
*G06Q 30/02* (2023.01)
*G06Q 20/36* (2012.01)
*G16H 40/60* (2018.01)

(52) U.S. Cl.
CPC ............. *G16H 40/60* (2018.01); *G16H 40/67* (2018.01); *G16H 80/00* (2018.01); *H04L 9/3239* (2013.01); *H04L 9/50* (2022.05); *H04L 2209/56* (2013.01)

(56) References Cited

U.S. PATENT DOCUMENTS

| | | | | |
|---|---|---|---|---|
| 2008/0222042 A1* | 9/2008 | Moore | ................... | G16H 20/10 235/375 |
| 2010/0169218 A1* | 7/2010 | Wang | ................... | G16H 20/10 705/50 |
| 2011/0071847 A1 | 3/2011 | Keresman, III et al. | | |
| 2013/0179180 A1* | 7/2013 | Patra | ...................... | G06Q 10/00 705/2 |
| 2013/0297333 A1 | 11/2013 | Timmons et al. | | |
| 2014/0006048 A1* | 1/2014 | Liberty | ............... | G06Q 30/0241 705/2 |
| 2014/0039911 A1* | 2/2014 | Iyer | ..................... | G06Q 30/0207 705/2 |
| 2014/0180809 A1* | 6/2014 | Boal | .................. | G06Q 30/0251 705/14.49 |
| 2015/0081330 A1* | 3/2015 | Mann | ..................... | G16H 20/13 705/3 |
| 2015/0332283 A1* | 11/2015 | Witchey | ................. | G16H 10/60 705/3 |
| 2017/0161713 A1* | 6/2017 | Feng | ..................... | G06Q 20/32 |
| 2017/0329922 A1* | 11/2017 | Eberting | ................ | G16H 40/67 |
| 2018/0060496 A1* | 3/2018 | Bulleit | .................. | H04L 9/0643 |
| 2018/0096175 A1* | 4/2018 | Schmeling | ............ | G06F 1/3206 |
| 2018/0165588 A1* | 6/2018 | Saxena | .................. | G06N 5/043 |
| 2018/0181964 A1* | 6/2018 | Zagarese | .......... | G06Q 20/40145 |
| 2018/0204195 A1* | 7/2018 | Kang | ..................... | G06Q 20/36 |
| 2018/0240539 A1* | 8/2018 | Doherty | ................ | G16H 20/10 |
| 2018/0253682 A1* | 9/2018 | Gilman | ................. | G06Q 20/28 |
| 2018/0293574 A1* | 10/2018 | Sooudi | .................. | G16H 20/10 |
| 2018/0308566 A1* | 10/2018 | Dempers | ................ | G06F 16/27 |
| 2019/0198144 A1* | 6/2019 | Blackley | ............... | G16H 20/10 |
| 2020/0082387 A1* | 3/2020 | Salama | ............. | G06Q 20/3674 |

\* cited by examiner

1200

1202
My Prescription — karbaflozin 20 mg
Quantity — 30 tablets
Directions — Take one tablet each morning with food
Prescriber — Dr. Molly
Date Prescribed — 10/17/2018
Fills Available — !2 before 10/17/19
Previous Fills — none
Pill Image — 123  ABC

1204

1206
Location 1
Distance 1.4 miles
1234 1st St.
9:00AM-9:00PM
Phone Number
Cost
$X
Send Rx Location 2
Distance 2.4 miles
8888 8th St.
8:00AM-9:00PM
Phone Number
Cost
$Y
Send Rx Location 3
Distance 2.2 miles
1111 11th St.
8:00AM-7:00PM
Phone Number
Cost
$Z
Send Rx Location 4
Distance 3.2 miles
9999 Big St.
9:00AM-9:00PM
Phone Number
Cost
$W
Send Rx

FIG. 10

METHODS AND SYSTEMS FOR PATIENT CONTROL OF AN ELECTRONIC PRESCRIPTION

CROSS REFERENCE TO RELATED APPLICATIONS

The present application claims priority to U.S. Provisional Patent Application No. 62/752,943, entitled "METHODS AND SYSTEMS FOR PATIENT CONTROL OF AN ELECTRONIC PRESCRIPTION", filed on Oct. 30, 2018. The entire contents of the above-listed application are hereby incorporated by reference for all purposes.

FIELD

The present description relates generally to an online system configured to allow a patient to maintain control of their prescription and its refills.

BACKGROUND AND SUMMARY

A prescriber may provide a paper prescription to his or her patient, when deemed medically necessary, where the patient may fill the prescription at a pharmacy of their choosing. The patient may shop, whether online, over-the-phone, or in-person, around to find a low price or quickest fill time. The paper prescription and its refills may be under the control of the patient until the prescription is relinquished to the pharmacy to be filled. Thus, once a pharmacy is selected, the patient may not be able to select a different pharmacy should their circumstances change for a current fill of the prescription or a future refill. In this way, the prescription may become the property of the pharmacy, wherein the patient loses control of the prescription. A process for the patient to transfer control of the prescription (and its remaining refills) to another pharmacy may be difficult and time consuming.

As an alternative to paper prescriptions, the prescriber may relay a prescription to a pharmacy electronically without the patient having control of the prescription. The healthcare provider may send the prescription via facsimile, telephone, and/or internet. While this may ameliorate some of the downsides associated with paper prescriptions, including duplication of prescriptions, prescription tampering, prescription forgery, loss of the paper prescription, and/or incorrect prescription filling due to illegible handwriting, electronic prescription filling may not be ideal for the patient as they may not shop the prescription to determine a best price or a location convenient to their plans following the prescriber visit. As such, current systems and methods for electronic prescriptions may not allow the patient to control the prescription. Furthermore, electronic prescriptions may share similar issues with paper prescriptions in that the patient may not decide to easily change pharmacies for future refills.

The inventors have found some additional issues associated with the previous examples described above common to both paper and electronic prescriptions. For example, prescribers may be involved with providing the prescription to a pharmacy, which may force the patient to quickly select a pharmacy while visiting the prescriber, which may prevent the patient from researching pharmacies for a low price and convenient location in an effort not to waste the prescriber's time. Furthermore, the pharmacy selected may be out of an insurance network of the patient, which may not be realized until the patient arrives to receive their prescription. Additionally, a prescriber's evaluation of the patient may be independent of insurance requirements for financial coverage of a prescription. That is to say, some insurance plans may demand information from one or more exams conducted by the prescriber for the insurance company to cover the cost of a prescription. However, the previous examples described above do not inform the prescriber of a patient's insurance requirements for financial coverage of a prescription. Additionally or alternatively, pharmacies may be forced to request refills and transfer the prescription if requested by the patient, resulting in an undue burden on the pharmacy, which may delay filling of other prescriptions. Lastly, a prescriber may be unaware of drugs and dosages thereof prescribed in different states or from different providers, which may result in prescription tampering, duplication, or drug-drug interactions.

Thus, a demand for a system for a patient to have control of their current prescription and refills thereof while mitigating a likelihood of fraud and incorrect prescription filling is still desired. In one example, the issues described above may be addressed by a method for tracking execution of a prescription prescribed by a prescriber, the method comprising receiving a prescription from a prescriber, correlating the prescription to a patient profile stored in a database, sending the prescription to a pharmacy, paying for the prescription with payment information associated with the patient profile, and updating the patient profile. In this way, the patient may control an outcome of the electronic prescription during each filling event (e.g., initial fills as well as any subsequent refills) of the prescription.

As one example, the patient may select a first pharmacy to initially fill the prescription via requesting to fill the prescription uploaded to their profile on a central server. The patient may maintain the selection or may change the selection to a second pharmacy different than the first pharmacy via the central server for subsequent refills. The patient may change the selection without directly contacting the pharmacy or their prescriber, thereby saving the patient and prescriber time. The central server may communicate to the pharmacy regarding the change in selection. By doing this, the patient may maintain control of the electronic prescription throughout a longevity of the prescription even after requesting to fill the initial prescription at a pharmacy. Additionally, the patient's profile may comprise pertinent data associated with the patient's medical history, concomitant medications, insurance coverage, and the like. In one example, the central server may inform the prescriber of the patient's insurance policy upon receiving a prescription such that the prescriber may execute the desired evaluations of the patient for the patient to receive financial coverage of the prescription.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 10 illustrates an example user interface of an application for filling a prescription that includes purchase options for different pharmacies.

DETAILED DESCRIPTION

Figure 1:
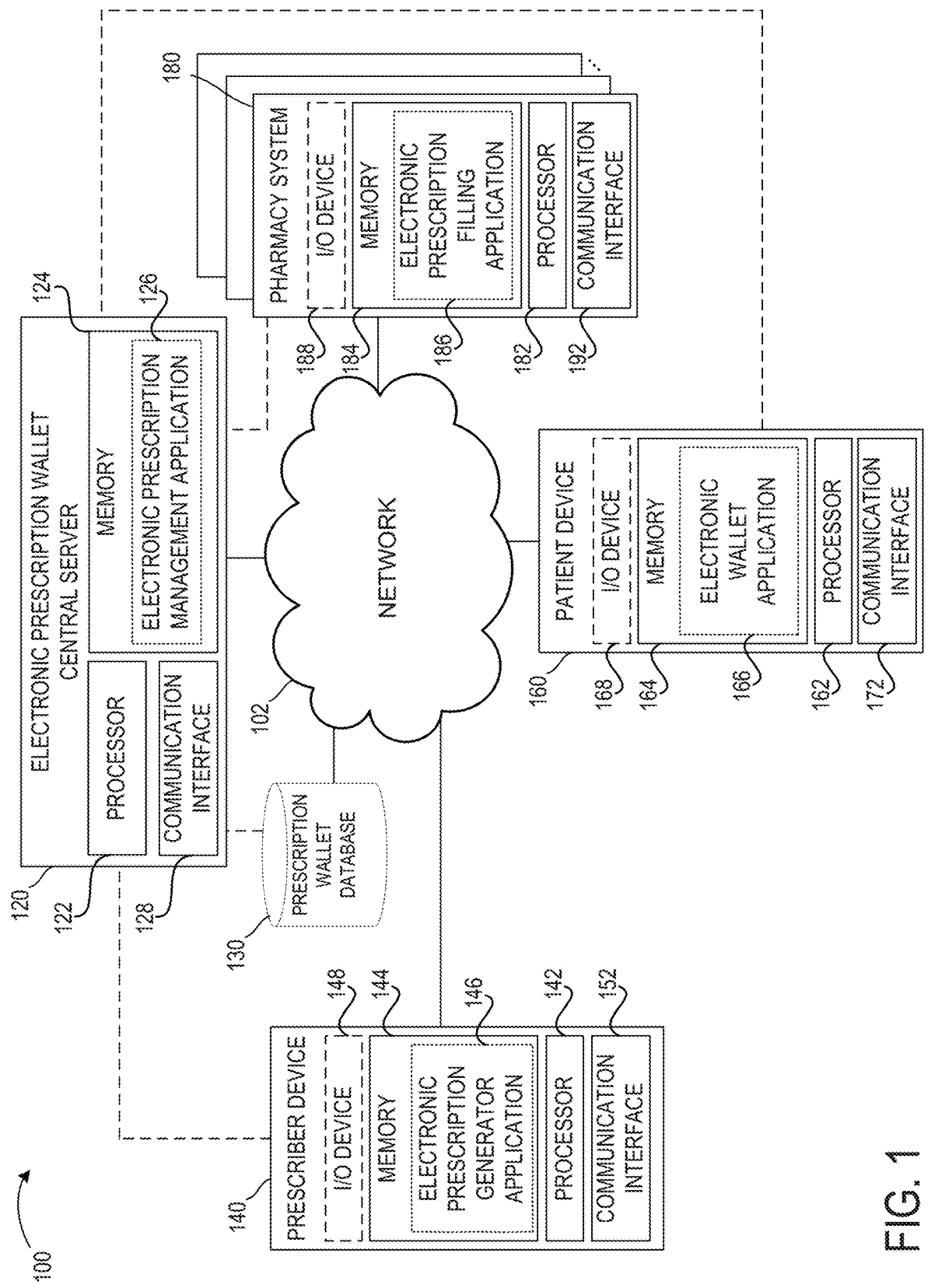
FIG. 1 illustrates an example of a system including a central server configured to communicate with a patient device, a prescriber device, and one or more pharmacy systems to manage electronic prescriptions.
Figure 2:
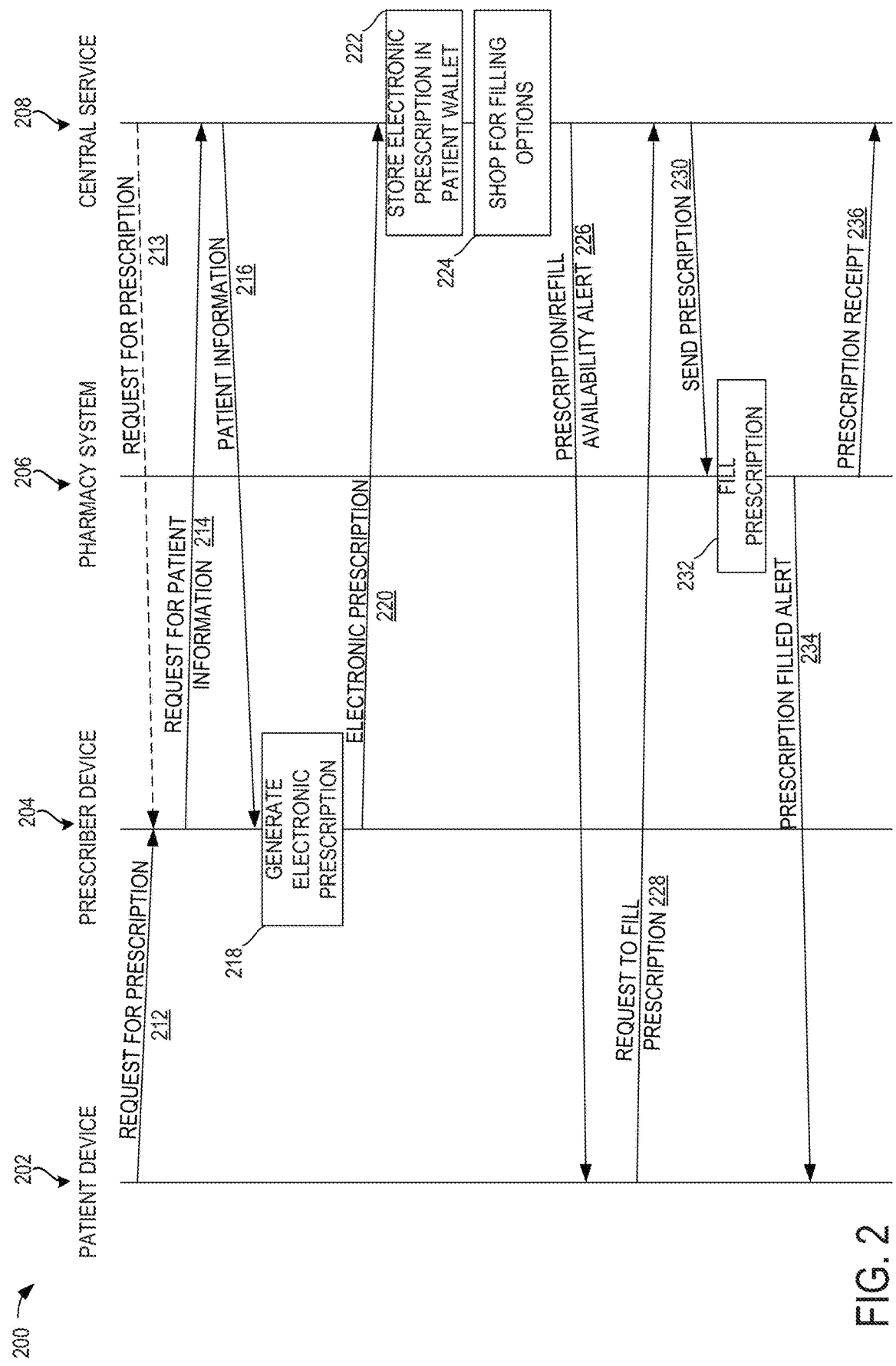
FIG. 2 illustrates a communication diagram for example communications between a patient device, a prescriber device, a pharmacy system, and a central server.
Figure 3:
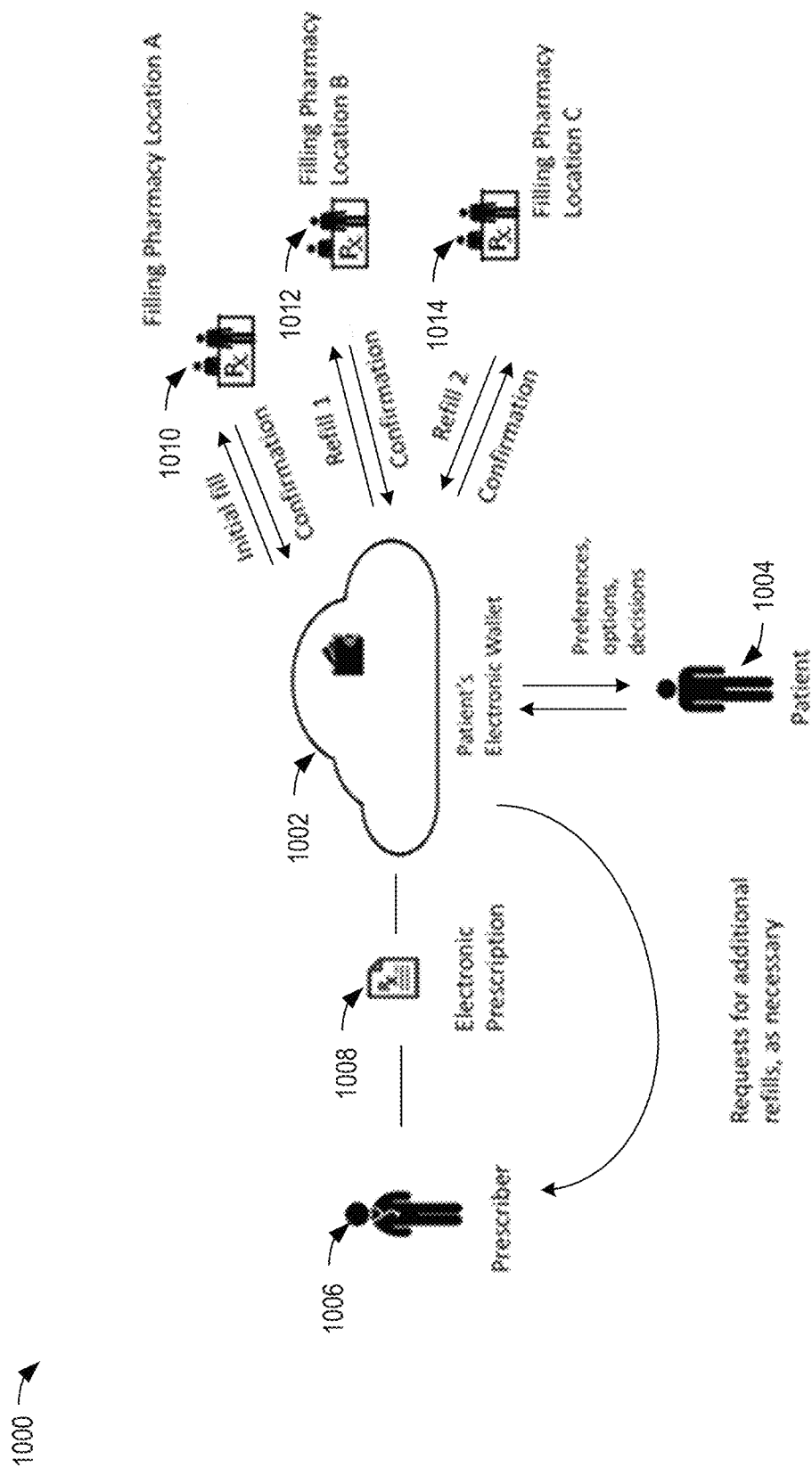
FIG. 3 illustrates an example process overview for electronic prescription management.
Figure 5:
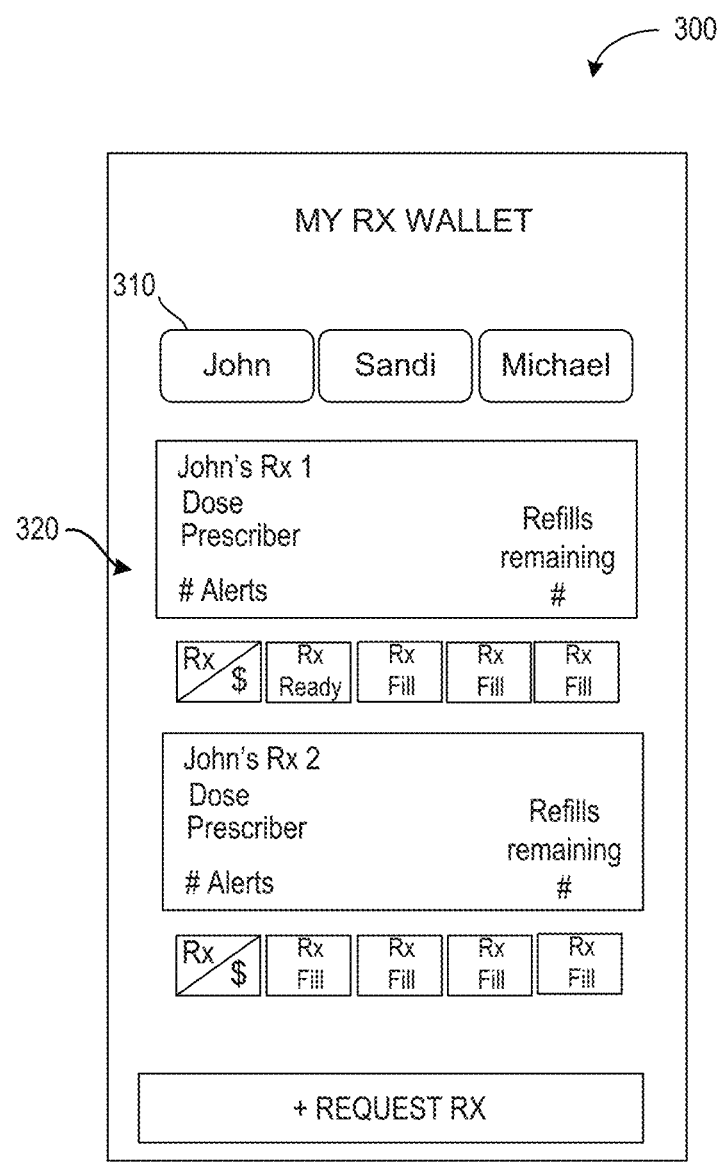
FIG. 5 illustrates an example user interface showing a patient profile.
Figure 11:
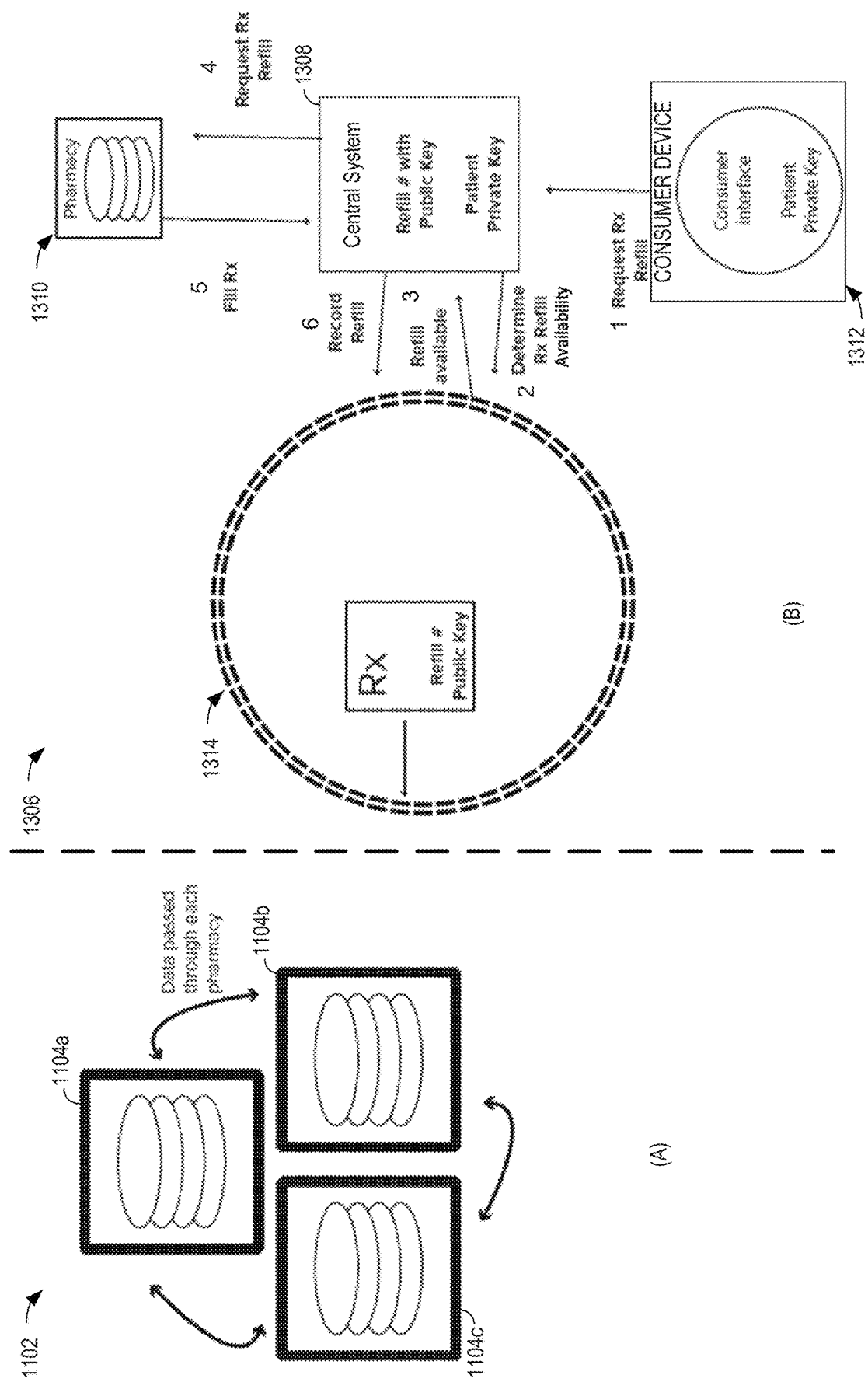
FIG. 11 illustrates example approaches for securing transmissions of data relating to managing prescriptions.

The following description relates to systems and methods for a patient maintaining control of a prescription assigned thereto, wherein the patient leverages control over the prescription until the prescription runs out. A prescription may be electronically submitted by a prescriber to a central server as shown in FIG. 1. A central server and/or one or more of the other systems disclosed herein may comprise a controller (e.g., a processor) configured to execute one or more methods, such as the methods of FIGS. 6, 7, 8, and 9, via instructions stored on memory thereof. The controller may further update various data on the central server and/or a memory storage device. An electronic prescription may be assigned to a profile of a patient, an example of which is shown in FIG. 5, wherein the patient may assume ownership of the prescription. The electronic prescription may include unique identifiers, validating its uniqueness and authenticity so that the prescription may not be duplicated. In some examples, a patient may select different pharmacies during different filling events of the prescription, as shown in FIG. 3. Additionally or alternatively, the patient may change a selected pharmacy during a single filling event of the prescription. In this way, the patient may maintain control of the prescription during a totality of the prescription with minimal to zero intervention from the prescriber and/or the pharmacy, thereby saving time and reducing costs. In some examples, a central server/service may automatically shop the electronic prescription by retrieving filling costs for the prescription from multiple pharmacies. The associated purchase options for the electronic prescription may be presented to the user, as shown in FIG. 10, to assist the user in selecting a pharmacy at which the electronic prescription is to be filled. Other features of an electronic prescription wallet and associated management system will be described herein, including features that contribute to: the security of data transmitted between devices, the tracking of electronic prescriptions and associated refills, and other features that help a patient retain control over associated prescriptions while increasing patient convenience and control over filling and storing the prescriptions. FIG. 2 illustrates a communication diagram for example communications between a patient device, a prescriber device, a pharmacy system, and a central server. FIG. 11 illustrates example approaches for securing transmissions of data relating to managing prescriptions.

Herein, methods and systems for a patient to control an electronic prescription are described. As described above with regard to the previous examples for electronic and paper prescriptions, the patient may comprise limited to no control over other prescription processes. In the circumstance of a paper prescription, the patient may shop the prescription via calling pharmacies and/or the internet, but relinquishes control of the prescription once provided to the pharmacy for filling. Additionally, paper prescriptions may be lost, forged, and/or difficult to decipher due to poor handwriting, which are only some of the downsides of paper prescriptions. Electronic prescriptions, which may overcome some of the downsides described for paper prescriptions, are prone to still other downsides. Electronic prescriptions along with associated subsequent valid refills may be owned by a pharmacy immediately following transmission from a prescriber, thereby preventing the patient from having control of the prescription to compare prices and/or convenience from being able to select from a group of pharmacies.

In either case of paper or electronic prescription, the patient may face an undue burden to change pharmacies if desired. The patient may contact the pharmacy currently in control of their prescription and request to transfer the prescription to another pharmacy. Contacting the pharmacy may be time consuming as there is no financial incentive for the pharmacy to efficiently transfer the patient's prescription. Furthermore, a number of times the patient may transfer the prescription and any refills may be limited by law. Still further, the pharmacy may be accountable for maintaining records of the prescription, including fill amount, and may be demanded to maintain physical copies of the prescription. Such a process may be burdensome for the pharmacy and the patient.

The present disclosure at least solves some of the issues described above with regard to electronic and paper prescriptions. The present disclosure relates to a third party system to which the prescriber may transmit a prescription. In one example, the third party system includes a patient-directed electronic prescription wallet (PDEPW). The PDEPW may receive an electronic prescription from a prescriber assigned to a patient wallet associated with a patient. The electronic prescription may comprise patient data so that the PDEPW may correlate the electronic prescription to the patient wallet associated with the patient. A patient device may send a request to shop the electronic prescription at one or more pharmacies, wherein shopping the electronic prescription may include the PDEPW sending the electronic prescription or information pertaining to the electronic prescription (e.g., an indication of the type, brand, quantity, etc. of the medication to be filled, optionally without any patient-identifying information) to a plurality of pharmacy devices (associated with different pharmacies) or other sources and/or databases (e.g., a centralized database) of pharmacy medication costs, the plurality of pharmacy devices sending bids or estimates to the PDEPW, and the PDEPW updating the patient wallet to include to the plurality of bids and estimates. The patient device may send a request to fill the electronic prescription at a selected pharmacy, and, (e.g., in response), the PDEPW may send (e.g., transmit) a single instance of the electronic prescription to a pharmacy device corresponding to the selected pharmacy where the electronic prescription is requested to be filled. Subsequent valid potential refills of the prescription may be maintained within the PDEPW, to be transmitted to another pharmacy (if the patient wishes to change the location of subsequent refills of the prescription) upon designation by the patient. Such subsequent transmissions may be scheduled for future fills and/or maintained in the PDEPW.

The PDEPW may be responsible for maintaining a unique, indelible record of the prescription and any remaining refills of the prescription, if applicable, and transmitting the prescription to a pharmacy (e.g., in response to a request from the patient and/or another triggering event). The PDEPW may maintain a history of the prescription, transmission, additional refills, date, time, and/or location of pharmacy at which the prescription was filled. Some health plans dictate that medications are to be filled at different pharmacies. For example, "specialty" medications may only be designated to be filled at a health plan's designated specialty pharmacy, while chronic medications may only be designated to be dispensed from a pharmacy benefit manager's mail-order facility, and a person who is acutely ill may pick up pain medication or antibiotics from a corner drug store. In such a scenario, a patient may be directed to use multiple pharmacies with no availability for the dispensing pharmacists at each pharmacy to know decisively what medications the patient is taking. The PDEPW may address the above situation by maintaining all prescriptions from all pharmacies (and optionally further patient information, such as information from a recent healthcare visit in which the patient was diagnosed with an acute illness), and transmit information about not only previous fills of the current medication, but also any other medication that the patient has taken and may currently be on (e.g., based on the patient information and the electronic prescriptions stored in the patient's electronic prescription wallet). The above centralized management of electronic prescriptions (and patient information) allows for coordination of medications to allow for drug interaction checking and medication regimen optimization. Additionally, the PDEPW may be internet based, wherein the medical history stored in a memory of the PDEPW may be analyzed by qualified prescribers or regulators across different country borders and state lines, further decreasing a likelihood of prescription abuse and fraud.

The PDEPW may be configured such that only a prescriber device may create or alter the prescription, which may include assigning or altering a dosage and a drug. In this way, the pharmacy system and/or the patient device may be prohibited from altering the prescription. The pharmacy system may confirm receipt of the electronic prescription. The pharmacy which filled the prescription may only exhibit control of the prescription in that instance and may not exhibit control of the prescription for future refills unless requested by the patient.

Thus, the methods and systems of the present disclosure may allow a patient device to direct a refill of the prescription to be filled at a first pharmacy once an electronic prescription is uploaded to a patient wallet. The patient device may select a second pharmacy to refill the prescription (e.g., for a subsequent prescription refill) without transferring the prescription from the first pharmacy that filled the prescription previously. In this way, the patient device may not contact the first pharmacy during subsequent refills of the prescription.

Turning now to FIG. 1, an electronic prescription management system 100 is shown, including a plurality of devices configured to generate, process, store, transmit, and/or otherwise manage electronic prescriptions of medications. As shown in FIG. 1, one or more devices, such as a prescriber device 140, a patient device 160, and one or more pharmacy systems 180, may be communicatively connected to a network 102, such that each of the prescribed device 140, the patient device 160, and the pharmacy system(s) 180 may remotely communicate with an electronic prescription wallet central service 120. The description of features relating to the one or more pharmacy systems 180 herein may be directed to a single pharmacy system for conciseness, but may be understood to be applicable to all or a subset of the pharmacy systems 180 in some examples.

The prescriber device 140, the patient device 160, and the pharmacy system 180 may include a personal/desktop computer, a portable computer (e.g., a laptop, a tablet, and the like), and/or a mobile device (e.g., a cellular phone, a smart phone, a personal data assistant, and the like). The network 102 may comprise one or more interconnected communication networks, including for example, a cellular communication network, a local area network (LAN), a wide area network (WAN), a public network (e.g., the Internet), an enterprise private network, and/or combinations thereof. Network/communication interfaces of the electronic prescription wallet central service 120, the prescriber device 140, patient device 160, and pharmacy system 180 may employ one or more suitable communication protocols defining rules and data formats for exchanging information and communicating over the network 102, such as User Datagram Protocol/Internet Protocol (UDP/IP), and/or Transmission Control Protocol/Internet Protocol (TCP/IP). The electronic prescription wallet central service 120, the prescriber device 140, patient device 160, and pharmacy system 180 may connect to the network 102 via a hardwired link, such as an IEEE 802.3 (Ethernet) link, a wireless link using a wireless network protocol, such as an 802.11 (Wi-Fi) link, and/or any other suitable link for interfacing with the network 102. In some examples, the electronic prescription wallet central service 120 may connect to the prescriber device 140, patient device 160, and/or pharmacy system 180 via a direct hardwired or wireless link.

The prescriber device 140 may include at least one processor 142 for executing one or more instructions stored in memory 144. That is to say, the memory 144 may store computer-readable instructions that when executed by the processor 142 cause components of the prescriber device 140 to perform one or more operations as will be described herein. An example of instructions stored in memory 144 includes an electronic prescription generator application 146.

The memory 144 may represent random access memory (RAM) comprising the main storage of a computer, as well as any supplemental levels of memory, e.g., cache memories, non-volatile or backup memories (e.g., programmable or flash memories), mass storage memory, read-only memories (ROM), etc. In addition, the memory 144 may be considered to include memory storage physically located elsewhere, e.g., cache memory in any computing system in communication with the prescriber device 140, as well as any storage device on any computing system in communication with the prescriber device 140 (e.g., a remote storage database, a memory device of a remote computing device, cloud storage, etc.).

The prescriber device 140 further comprises an input/output device 148 and a communication interface 152. The input/output device 148 of the prescriber device 140 may be configured to receive data from input sources and output data to output sources, thereby serving as an interface between the input sources, the output sources, and the prescriber device 140. For example, the input device 148 may receive input data from a user input device such as a keyboard, mouse, microphone, touch screen/touch pad, and other such user input devices, and the input/output device 148 may output data to one or more user output devices such as a display (e.g., a computer monitor), a touch screen, speakers, and/or other such output devices that may be used to output data in a format understandable to a user. As such, in some examples, the processor 142 of the prescriber device 140 may execute stored instructions using information (e.g., user input data) from the input/output device and may control an output device by sending instructions to the input/output device 148 based on an execution of the stored instructions. It is to be understood that the user input device(s) and/or the user output device(s) may be integrated with the prescriber device and/or may include peripheral devices communicatively connected to the prescriber device.

Electronic prescription generator application 146 may comprise code that when executed by the processor 142 facilitates interfacing between a user of the prescriber device 140 and the electronic prescription wallet central service 120. For example, a user, such as a medical doctor, physician assistant, nurse practitioner, nurse, medical assistant, dentist, and/or other qualified user, may input data (e.g., via an input device interfacing with input/output device 148) for generation of an electronic prescription for a particular patient. The electronic prescription generator application 146 may process the input data, generate an associated electronic prescription, and control the communication interface 152 to transmit the electronic prescription to the electronic prescription wallet central service 120 (e.g., via network 102).

The electronic prescription wallet central service 120 may comprise at least one processor 122 for executing one or more instructions (e.g., stored in memory 124) to perform and/or cause components of the electronic prescription wallet central service 120 to perform one or more operations. The electronic prescription wallet central service 120 may further comprise the memory 124 and an electronic prescription management application 126 stored thereon.

The electronic prescription management application 126 may comprise code that when executed by the processor 122 controls the service 120 (e.g., a communication interface 128) to receive output data from the prescriber device 140, the patient device 160, and/or the pharmacy system 180. For example, the memory 124 comprises computer-readable instructions (e.g., including electronic prescription management application 126) that when executed by the processor 122 control the service 120 to receive the electronic prescription generated and transmitted by the prescriber device 140. The electronic prescription may then be automatically transmitted by the electronic prescription wallet central service 120 to a prescription wallet database 130. The electronic prescription wallet central service 120 may comprise the communication interface 128, which may be substantially similar to communication interface 152 of the prescriber device 140.

The prescription wallet database 130 may represent a storage device (or linked storage devices) that is local or remote relative to the electronic prescription wallet central service 120. The prescription wallet database 120 may comprise a plurality of databases, including a prescriber database, a patient database, a pharmacy database, a rules database, and the like.

The prescriber database may include data associated with a prescriber, including but not limited to a prescriber's name, the prescriber's title at a healthcare facility, one or more government-issued or facility-issued identification numbers associated with the prescriber, patients associated with the prescriber, healthcare facilities at which the prescriber visits patients, personal information for the prescriber (e.g., address, phone number, etc.), and/or any other such relevant information. The prescriber database may also include prescriber credentials, such as a user name and a password or personal identification number (PIN) that is assigned to the user name, for use in accessing the application server and/or verifying a prescriber's identity.

The patient database may store one or more patient records. Each of the patient records may be associated with a particular patient and include data indicating the patient's name, address, personal data (e.g., age, date of birth, gender, social security number, etc.), one or more prescribers associated with the patient, the facility or facilities at which the patient is a resident, insurance information for the patient, allergies of the patient, medications prescribed to the patient, medical history of the patient (e.g., diagnosed illnesses, operations performed on the patient, health events for the patient, etc.), and/or other such information that may be relevant for a healthcare facility, a prescriber, and/or a pharmacy.

The rules database may comprise a plurality of prescription rules. The prescription rules may include rules for prescribing medications for geographic regions and may vary among different geographic regions. For example, in the United States, the rules database may store prescription rules of each state and/or U.S. territory that has specific laws or regulations as well as any federal laws/regulations related to the electronic prescribing of medications. Each prescription rule may include data indicating the particular laws and/or regulations for electronic prescribing for a particular geographic region in a format that may be read by the processor 122, and the electronic prescription management application 126 may perform one or more operations based on the retrieved prescription rule(s) for a particular geographic region. A prescription rule for a particular geographic region may include data for different types of facilities for the particular geographic region. For example, a particular state may have different electronic prescription laws/regulations for long term care facilities and hospitals, as such, depending on the type of facility that a patient is receiving care in, the electronic prescription wallet central service 120 may interface with the prescriber device 140 differently such that the correct rules/regulations for the geographic region and type of facility are enforced in the generation of an electronic prescription for the patient. Prescription rules for different geographies may also include the option for a secondary prescriber to alter, modify, and/or assign changes to the prescription. The rules database may also include preferences or options selected by a patient to control how electronic prescriptions for that patient are managed (e.g., storage parameters, permissions for accessing/editing/transmitting/receiving electronic prescriptions, etc.).

In one example, the prescriber device 140 may transmit an electronic prescription to the electronic prescription wallet central service 120 in a manner described above. The electronic prescription is received by the electronic prescription wallet central service 120, wherein the electronic prescription is correlated to a patient profile stored in the prescription wallet database. The correlation may include matching patient data transmitted with the electronic prescription (e.g., name, social security number, and the like) to data stored in the patient database of the prescription wallet database. The electronic prescription wallet central service 120 may further look-up regional rules in the rules database associated one or more of a residence of the patient and/or location of the prescriber. The electronic prescription wallet central service 120 may flag the electronic prescription in the event that the prescription violates one or more regional rules. Additionally or alternatively, the electronic prescription wallet central service 120 may send a message to the prescriber device 140 indicating a violation has occurred.

The patient device 160 may be configured similarly to the prescriber device 140 in that the patient device 160 comprise a processor 162, a memory 164, an I/O device 168, and a communication interface 172 which may be substantially similar to the processor 142, memory 144, the I/O device 148, and the communication interface 152, respectively. However, an electronic prescription application 166 stored on memory 164 may be different than electronic prescription generator application 146.

The electronic prescription application 166 may comprise program code that when executed by the processor 162 facilitates interfacing between the patient device 160 and the electronic prescription wallet central service 120. A patient may input data via the I/O device 168 of the patient device 160 (e.g., via an input mechanism such as a touch screen, keyboard, voice detection system, etc. in communication with the I/O device 168). The processor 162 may execute computer-readable instructions stored in the memory 164 to control the patient device 160 to send patient data and/or patient requests to the electronic prescription wallet central service 120 (e.g., via the communication interface 172).

As another example, the patient device 160 may send a request to access a patient profile. The request may include patient data and/or login information including a username and password and/or identification pin associated with the username. The electronic prescription wallet central service 120 may receive the request and correlate the patient data and/or login information included in the request to a patient profile stored in the prescription wallet database 130. The electronic prescription wallet central service 120 may authorize access to the patient profile, where one or more updates and/or requests may be executed.

For example, once access is granted, a patient using the patient device 160 may update patient data stored thereon including address, health insurance, dependents, and/or payment information. Payment information may include one or more payment preferences including physical and electronic payment preferences, wherein electronic payment preferences may include an electronic payment source stored to the patient profile. In one example, the electronic payment source may include credit card information, debit card information, bank routing information, and/or the like. In this way, if patient preferences associated with the patient profile are adjusted to indicate a desire to electronically pay for prescription(s), then the electronic prescription wallet central service 120 may send payment information to a pharmacy when requesting the pharmacy to fill a prescription on behalf of the patient. Other patient preferences that may be updated may include pharmacy preferences which may include one or more parameters for the electronic prescription wallet central service 120 to include during requests for an electronic prescription, wherein the parameters may include a prescription cost at a pharmacy, a pharmacy vicinity to a patient's residence and/or current location, a desired operating hour range, and/or prescription availability.

Additionally or alternatively, if the patient device 160 is granted access to the patient profile, then one or more requests may be sent from the patient device 160 to the electronic prescription wallet central service 120. The requests may include one or more of a request to fill the prescription at a desired pharmacy, request to shop the prescription to a plurality of pharmacies meeting one or more parameters set by the patient, and/or a request to change a pharmacy for a refill of a prescription from a pharmacy at which the prescription was last filled to a different pharmacy. The shopping feature may include either actually soliciting bids from pharmacies or creating pricing estimates from data sources that are not directly affiliated with the pharmacy. In one example, the electronic prescription wallet central service 120 may retrieve a list of pharmacies which meet one or more patient preferences as dictated in the patient profile, wherein the list of pharmacies may be displayed to the patient profile and/or to another user interface (e.g., of the electronic wallet application 166) presented on the patient device. The electronic prescription wallet central service 120 may receive a request sent by the patient device 160 to fill the prescription at a pharmacy included in the list of pharmacies or to a different pharmacy not included in the list (e.g., entered by the patient via the patient device). Additionally or alternatively, the patient device 160 may send a request to shop the electronic prescription to the pharmacies included in the list of pharmacies, wherein the electronic prescription wallet central service 120 may receive the request and send the electronic prescription to the plurality of pharmacies included in the list via the pharmacy systems 180. The electronic prescription wallet central service 120 may receive a plurality of bids or pricing estimates from the pharmacy system 180 corresponding to the plurality of pharmacies, and the plurality of bids or pricing estimates may be sent to the patient device 160. In some examples, the electronic prescription wallet central service 120 may perform ad hoc requests to pharmacies to receive bids or pricing estimates (e.g., based on a patient request for a particular prescription). In other examples, the electronic prescription wallet central service 120 may include or be in communication with a centralized database that creates estimates for costs of prescriptions at pharmacies (e.g., based on continuous or regular updates to bids or pricing estimates from the pharmacies). In such examples, the electronic prescription wallet central service 120 may access the centralized database in order to provide bids or pricing estimates for a prescription responsive to a request from a patient and/or when otherwise controlled to perform a shopping operation.

The pharmacy systems 180 may each comprise a processor 182, a memory 184, an electronic prescription filling application 186, an I/O device 188, and a communication interface 192. The processor 182, the memory 184, the I/O device 188, and the communication interface 192 may be substantially similar to the processor 142, memory 144, the I/O device 148, and communication interface 152 of the prescriber device 140, respectively.

The electronic prescription filling application 186 may be an example of computer-readable instructions stored on memory 184 that when executed enable the pharmacy system 180 to receive (e.g., via the communication interface 192) a request to fill a prescription or receive a request for a cost to fill a prescription. The processor 182 may generate and control the communication interface 192 to send a bid comprising information regarding the cost to fill the prescription and an approximation of when the prescription may be filled to the electronic prescription wallet central service 120 via the network 102. In one example, one or more of the pharmacy systems 180 may correspond to an individual pharmacy or to a group of identical or related pharmacies (e.g., pharmacies belonging to a franchise or chain of pharmacies).

The pharmacy system 180 may send a notification to the electronic prescription wallet central service 120 indicating a prescription is filled. The electronic prescription wallet central service 120 may receive the notification and forward the notification to a corresponding patient (and associated patient device) to which the electronic prescription is prescribed. Once the prescription is picked up by the patient or sent out to be delivered to the patient, the pharmacy system 180 may send a receipt to the electronic prescription wallet central service 120, wherein the receipt may comprise a time, a date, a location, and a cost of the prescription. If funds are still due for the prescription, then the receipt sent to the electronic prescription wallet central service 120 may further include a request for payment. The electronic prescription wallet central service 120 may access a patient's electronic payment information stored in conjunction with their patient profile and send the payment information to the pharmacy system 180 in accordance with patient preferences.

Turning now to FIG. 2, a routine 200 is shown illustrating a sequence of operations that may be performed by a patient device 202, a prescriber device 204, a pharmacy system 206, and a central service 208. The patient device 202 may be an example of the patient device 160 of FIG. 1. The prescriber device 204 may be an example of the prescribed device 140 of FIG. 1. The pharmacy system 206 may be an example of the pharmacy system 180 of FIG. 1. The central service 208 may be an example of the electronic prescription wallet central service 120 of FIG. 1.

The routine 200 may begin at 212, which comprises the patient device 202 sending a request for prescription to the prescriber device 204. Additionally or alternatively, the routine 200 may include the central service 208 sending a request for a prescription to the prescriber device 204, as indicated at 213. For example, the central service 208 may send the request for the prescription in response a current prescription being depleted along with an indication that a refill of the current prescription is desired. It is to be understood that the routine 200 may in still other examples begin with the prescriber device initializing a prescription generation (e.g., responsive to an in-person request for a prescription and/or responsive to another trigger, such as a scheduled prescription generation).

The prescriber device 204 may send a request for patient information at 214 to the central service 208 (e.g., responsive to receiving a request for a prescription from the patient/patient device 202 and/or the central service 208 and/or responsive to any other suitable trigger, such as part of an introductory setup when seeing a new patient). The request for patient information may include a request to view a patient profile which may provide current patient prescription, diagnosed diseases, allergies, and/or other patient information described above.

The central service 208 may send patient information at 216 to the prescriber device 204 following receipt of the request for patient information. The prescriber device 204 receives the patient information and may generate an electronic prescription for the patient associated with the patient information at 218. In some examples, the patient information may be used to guide the generation of the electronic prescription (e.g., the prescriber may select a prescription medication for the patient based on the patient information so as to adhere to patient preferences and/or avoid conflicts with patient allergies/conditions/other medications the patient is taking, etc.).

The prescriber device 204 may send the electronic prescription at 220 to the central service 208, where the central service stores the electronic prescription in a patient wallet associated with the patient corresponding to the patient device 202 at 222. The central service 208 may correlate the electronic prescription to the patient wallet via patient information included with the electronic prescription.

The central service 208 may (e.g., automatically or by request from the patient) shop for filling options at 224, which may be executed based on one or more parameters saved to a patient profile and/or a patient wallet. A prescription refill/availability alert is sent from the central service 208 to the patient device 202 at 226. The prescription refill/availability alert may include information to alert the patient that an electronic prescription (e.g., the electronic prescription requested at 212/213 and generated at 218) or a refill associated therewith is ready to be filled.

The patient device 202 may send a request to fill the prescription at 228 to the central service 208, wherein the central service 208 sends the electronic prescription, which may additionally comprise at least some patient data, to the pharmacy system 206 at 230. For example, the central service 208 may send the prescription to a pharmacy selected by the patient via the patient device 202 based on the shopping for filling options performed at 224 and communicated to the patient device at 226. The prescription is filled by the pharmacy system 206 at 232, and the pharmacy system 206 may send a prescription filled alert to the patient device 202 informing the patient of the availability of the filled prescription for pickup. At 236, the pharmacy system 206 may send a prescription receipt to the central service 208, wherein the prescription receipt may request payment from the patient wallet. In this way, the electronic wallet associated with the patient device and accessed via the central service may maintain the electronic prescription and only send the pharmacy system information needed for a requested filling of the electronic prescription. Accordingly, the patient may maintain control over the electronic prescription and reduce information that is provided to other entities while still being provided with a user-friendly mechanism for filling a prescription (e.g., relative to other prescription-filling mechanisms, which involve more directed input/effort on the patient's behalf, such as a patient going to a pharmacy in person to both request and pick up a filled prescription).

FIG. 3 shows an example system 1000 for managing prescription fills and refills at different pharmacies using an electronic wallet. For example, system 1000 may utilize and/or include one or more of the devices discussed above with respect to FIGS. 1 and 2 to manage an electronic prescription wallet 1002 for a patient 1004. As illustrated, the patient 1004 may update the electronic prescription wallet 1002 with user preferences and/or options (e.g., preferred pharmacies/physicians, location information for the patient, etc.) and may provide input (e.g., via a patient device, such as patient device 160 of FIG. 1) indicating decisions regarding the usage and/or maintenance of the electronic prescription wallet 1002. In one example, a decision may include a request for additional refills of a prescription in the wallet, where the request is input by the patient to update the electronic wallet, then forwarded from the electronic wallet to a prescriber 1006. The prescriber 1006 may provide input to a prescriber device (e.g., prescriber device 140 of FIG. 1) to generate an electronic prescription 1008 corresponding to the patient's request. The electronic prescription 1008 may be transmitted to the patient's electronic prescription wallet 1002 in order to update the available prescriptions for the patient stored therein.

As prescriptions may designate an initial fill and a number of eligible refills, the patient may prefer to utilize different pharmacies for different fills/refills of the prescription. Accordingly, pharmacy location A 1010 may handle the initial filling of the electronic prescription 1008. Responsive to a request to fill the prescription, the pharmacy location A 1010 may send a confirmation request to the electronic prescription wallet 1002 to validate the fill request and/or to confirm that the pharmacy will be handling the fill, and then provide the initial filling of the electronic prescription. At a later date, the patient may request and receive a first refill from a pharmacy location B 1012, which may perform a similar filling confirmation/validation as pharmacy location A 1010. At a still later date, the patient may request and receive a second refill from pharmacy location C 1014, which may also perform a similar filling confirmation/validation as pharmacy location A 101 and pharmacy location B 1012. In this way, the patient may be able to take advantage of particular cost-saving deals at different pharmacies for different prescription fills and/or select a pharmacy for a particular prescription fill based on current factors related to the patient (e.g., current location relative to the pharmacies).

Figure 4:
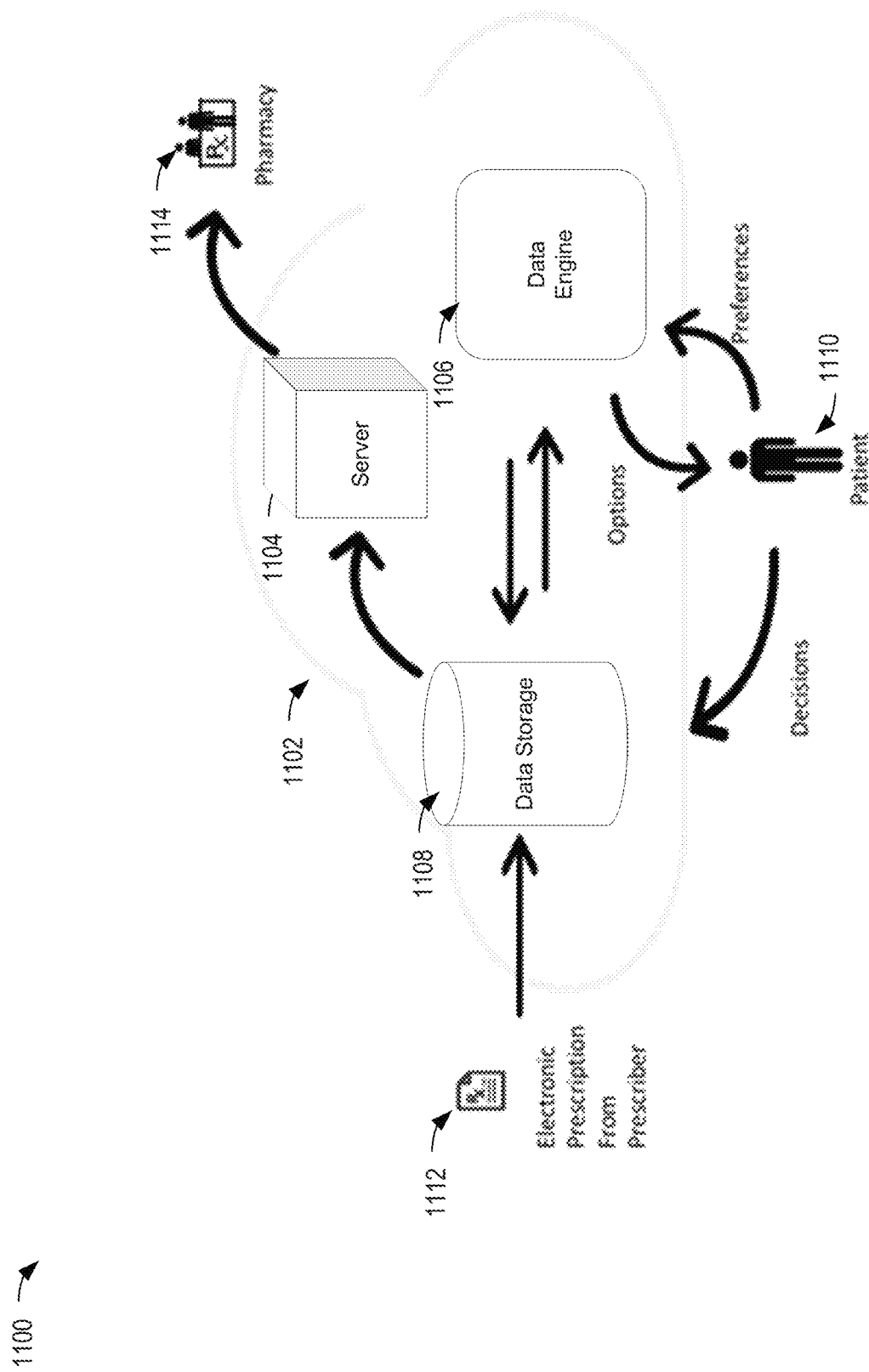
FIG. 4 illustrates an example detail view of an electronic prescription wallet system.

FIG. 4 shows an example schematic of an electronic prescription wallet 1102, such as electronic prescription wallet 1002 of FIG. 3. As shown, the electronic prescription wallet 1102 may include a server 1104, a data engine 1106, and a data storage 1108. The data engine may receive preference information from a patient 1110 associated with the electronic prescription wallet 1102 and provide options for the patient (e.g., where some of the patient's preferences may be responses to available options for customizing the patient's electronic prescription wallet). The data engine 1106 may communicate with a data storage 1108 to store the patient preferences (e.g., in association with a particular electronic prescription wallet account associated with the patient). In some examples, the data storage 1108 may store multiple electronic prescription wallet accounts for multiple users. Decisions made by the patient regarding an associated electronic prescription wallet may be stored at the data storage device 1108 and provided to the server 1104 and/or the data engine 1106 to implement electronic prescription management processes, examples of which are described herein. The data storage 1108 may also store an electronic prescription 1112 from a prescriber in association with the patient 1110 and provide the electronic prescription to the server 1104 for controlling the filling of the electronic prescription at a pharmacy 1114.

Turning now to FIG. 5, an embodiment of a profile 300 is shown. In one example, the profile 300 may correspond to the patient associated with patient device 160 of FIG. 1 and/or patient device 202 of FIG. 2. The profile 300 may comprise a first section 310 which may list family member associated with the patient. In one example, the family members associated with the patient may be covered by a shared insurance policy. As such, the patient may manage prescriptions for dependents via the profile 300. In this way, the patient may utilize a single login to access data related to themselves or others covered by the same insurance policy and/or other payment method.

Additionally or alternatively, the profile 300 may comprise a primary user authorized to make changes to the profile 300, wherein the changes may include adding secondary users, adjusting payment information, adjusting preferences, adjusting an address, and the like. The preferences may include ranking priorities for filling a prescription, wherein prioritization may be based on price, proximity, availability, wait times, and the like. The secondary users may not adjust settings associated with the profile 300. In some examples, the secondary users may only be authorized to select a pharmacy at which to fill a prescription. Additionally or alternatively, secondary users may update payment information The profile 300 may further include a second section 320 which may display prescription information. The prescription information may include a dose, name of the prescriber that prescribed the prescription, number of remaining refills, and a status of the prescription. The status of the prescription may include an option for the patient to request to fill the prescription, if the prescription is being filled but not ready for pick-up, and if the prescription is ready for pick-up. The prescription information may further include a price of previous fills of the prescription. In some examples, the price of previous fills may be shown against a national, regional, and/or local average cost of filling the prescription, wherein a difference between the two averages may be displayed. If the difference is a positive difference, wherein the patient paid less for the prescription than average, then the difference may be displayed in green. If the difference is a negative difference, wherein the patient paid more for the prescription than average, then the difference may be displayed in red.

In some examples, additionally or alternatively, the profile 300 may store other pertinent patient health data. For example, the profile 300 may display relevant allergies, previous complications with prescriptions, previous doses of the prescription, and the like. In some examples, the profile 300 may further illustrate blood pressure, heart rate, blood oxygen, cholesterol, and results of various organ function tests including kidney, liver, colon, lung, heart, brain, eye, ear, and the like. In this way, the prescriber, who may access the profile 300 of the patient, may prescribe the patient a prescription while ensuring that negative side-effects in response to the prescription may be mitigated.

Additionally or alternatively, the central server may cross-reference the prescription 122 to data corresponding to the profile to determine if any pertinent information is desired to be relayed back to the prescriber. For example, if the patient's insurance policy demands certain tasks to be executed in order for financial compensation and/or financial coverage of a prescription, then the central server may notify the prescriber once the prescription is uploaded of such tasks. As one example, if the prescriber 120 uploads a prescription 122 for a knee brace, then the controller 104 may analyze the patient's insurance and determine that financial coverage for the knee brace may be granted only in response to the prescriber performing one or more types of knee exams of the patient's knee. In this way, if the prescriber uploads the prescription while the patient is with the prescriber, then the prescriber may perform the various demands of the patient's insurance policy during the same visit so that the patient may receive financial coverage. Furthermore, this may prevent the patient from returning to the prescriber to perform the tasks demanded by the insurance policy to receive financial coverage, thereby saving the patient and prescriber time.

In one example, FIGS. 1 and 3 illustrate systems for tracking a patient prescription, wherein the tracking may occur via a central server comprising a controller or other processing device with instructions stored on memory thereon that when executed enable the controller to correlate data received from one or more local clients to a patient profile or other profiles saved in a database corresponding to the central server. The local clients may be computers or other computing devices different than the controller and/or the central server. The local clients may communicate with the central server via the Internet or other method.

In one example, a prescriber may input authenticating data (e.g., login information), including a username and password, wherein the central server may receive the authenticating data. The controller may correlate the authenticating data to a prescriber profile stored in the database. The prescriber may be permitted to input other data corresponding to their profile as allowed by the controller. In one example, the controller may signal to the local client of the prescriber to adjust a display of the local client to allow the prescriber to provide one or more inputs include patient data and prescription information. The prescriber may electronically input patient data and prescription information via their local client to the central server, wherein the controller may correlate the received data to a patient profile (such as the patient profile of FIG. 3). This may be correlate via a patient identification, which may include a patient name, policy number, social security number, and the like. Prescription information provided by the prescriber may be saved to the patient profile in the database.

The patient may login to their profile via a patient local client which may be different than the local client used by the prescriber. In one example, the patient may use an electronic device (e.g., a local client) different than an electronic device used by the prescriber. The controller may signal to display the patient profile to a display of the patient's local client in response to the login information provided by the patient being authenticated. Authenticating login information may include corroborating the provided login information with login information associated with a profile saved in the database. In response to the verification, the patient may access their profile, thereby allowing the patient to view the prescription. The central server may allow the patient to select a variety of option with regard to their prescription, including filling their prescription and comparing prices for filling their prescription. The controller may receive the desired action from the local client of the patient and execute accordingly. For example, if the patient decides to shop the prescription, the central server may send the prescription to a plurality of desired pharmacies, wherein the central server may receive a plurality of bids from the plurality of pharmacies. The controller may process the plurality of bids and correlate the plurality of bids to the patient profile. As such, a display of the patient profile may be adjusted to include the plurality of bids. The central server may further receive a request to fill the prescription at a pharmacy. As such, the central server may send a request to a pharmacy, which may include patient data including the prescription information, patient information, and patient payment information. The central server may receive confirmation of the prescription being filled once the patient has picked up the prescription. A record may be saved to the patient profile indicating a time, place, cost, and dosage of the prescription being filled.

The central server may be further configured transmit data regarding patient information to the prescriber in response to receiving a prescription. For example, if the prescription is a blood thinner, then the patient's health insurance may demand one or more blood tests be executed for financial coverage to occur. Stipulations demanded by the patient's health insurance may be saved to the database and associated with the patient's profile. As such, the online prescription system may automatically send, receive, and correlate data more efficiently than current methods.

Figure 6:
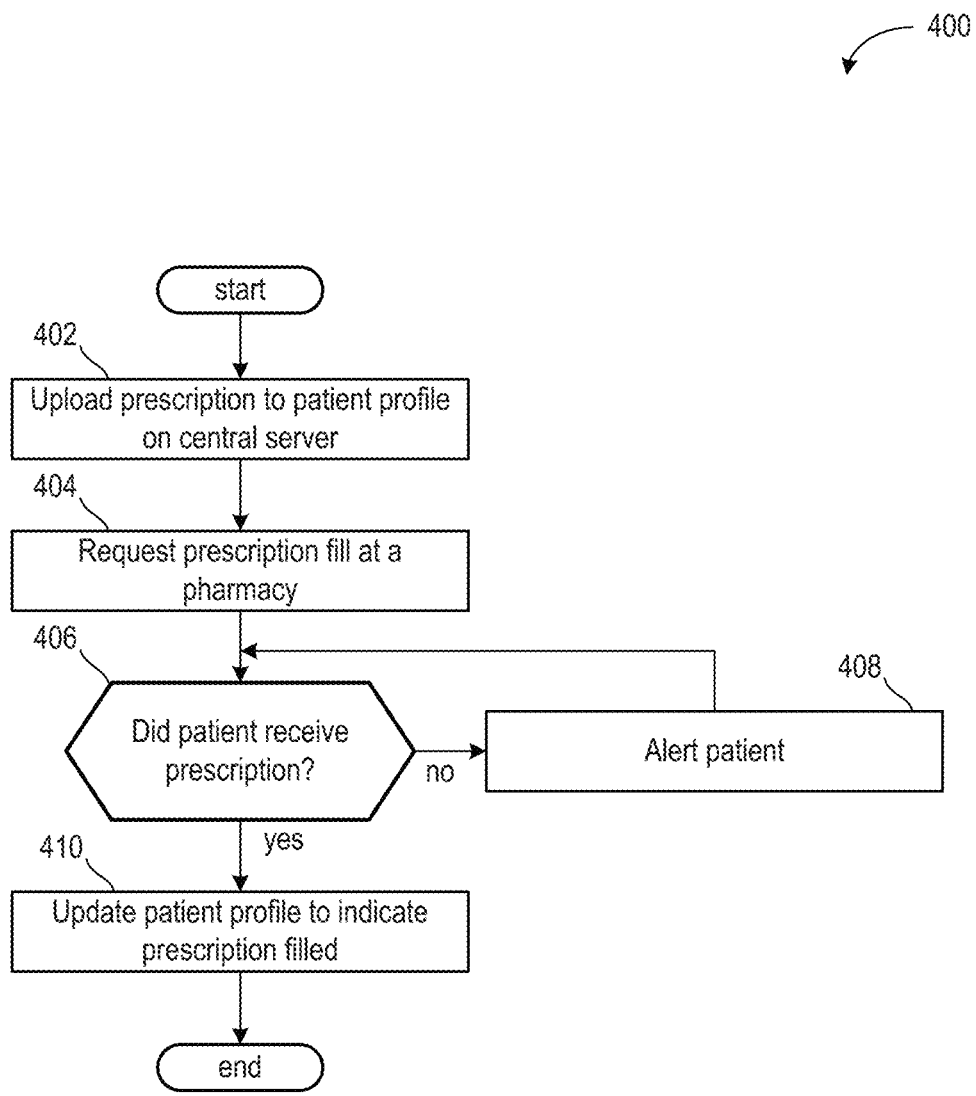
FIG. 6 illustrates a high-level flow chart illustrating an example method for receiving a prescription, filling a prescription, and updating information regarding the prescription.

Turning now to FIG. 6, it shows a high-level flow chart illustrating a method 400 for electronic filling a prescription. Instructions for the method 400 and the other methods included herein may be executed by the controller (e.g., processor 122 of FIG. 1). The controller may execute the one or more methods in response to feedback from one or more of the patient, prescriber, pharmacy(ies), and the central server.

The method 400 begins at 402, which include uploading a prescription to a patient profile on the central server. A prescriber may access their prescriber profile, which may include inputting login information and other authenticating data (e.g., identification number and the like) via a local client, wherein the local client relays the login information to the central server. The prescriber may input data referencing the patient, including a patient name, a patient identification number, a patient group number, and the like. This may allow the prescriber to update a portion of the profile of the patient (e.g., the second section 320 of FIG. 5) with the prescription. The prescriber may further include dosage, number of refills, and the like. Additionally or alternatively, the prescriber may include acceptable alternatives to the original prescription, wherein the alternatives may be used in place of the original prescription in the event of an outage or other limitation (e.g., cost too high). Once the prescriber (e.g., doctor, physician assistant, nurse practitioner, etc.) has uploaded the prescription to the central server, the controller may update the database to associate the prescription to the desired patient profile.

The method 400 may proceed to 404, which may include requesting a prescription fill at a pharmacy. The patient may select a pharmacy to fill the prescription via a local client, which may relay the information to the central server. In one example, one or more pharmacies may be displayed through a screen of the local client, which may include one or more of a smartphone, tablet, computer, and the like, wherein selection of the pharmacy may be relayed to the central server from the patient's local client. In some examples, the patient may request to receive prices from a plurality of pharmacies meeting one or more parameters, wherein the parameters may include proximity, cost, availability, and wait time. In one example, the central server may communicate with a plurality of local clients associated with different pharmacies to retrieve information desired by the patient (e.g., cost, proximity, availability, and wait time), wherein the central server may send the information to the patient's local client, thereby adjusting the display of the patient's local client. The patient may select a pharmacy through their local client, the request to fill the prescription at the selected pharmacy is relayed to the local client. This may occur outside an office of the prescriber. In this way, the patient may request to fill the prescription without a paper prescription. By doing this, the patient may save time by arriving to the pharmacy once the prescription is complete. Additionally, a pharmacist at the pharmacy may avoid deciphering a handwritten prescription note written by the prescriber.

The method 400 may proceed to 406, which may include determining if the patient received the filled prescription. The pharmacy may signal to the central server, via a local client, that the patient has received the prescription. In some examples, this may correspond to a charge to the profile of the patient. That is to say, once the patient receives the prescription, the pharmacy may request payment information from the central server, wherein the request may indicate the patient receiving the prescription. If the patient has not yet received the prescription, then the method 400 may proceed to 408, which may include alerting the patient that the prescription is prepared and ready to be received. In some examples, the prescriber may also be notified following a threshold duration elapsing between the prescription being ready to be received and the patient not yet receiving the prescription. In one example, the threshold duration may be equal to two days or more.

If the patient has received the filled prescription, then the method 400 may proceed to 410, which may include updating the patient profile to indicate the prescription is filled. The updating may further include date, time, location, payment information, and the like. Furthermore, the profile may be updated such that the prescription may comprise one fewer fill along with a cost of the prescription.

Figure 7:
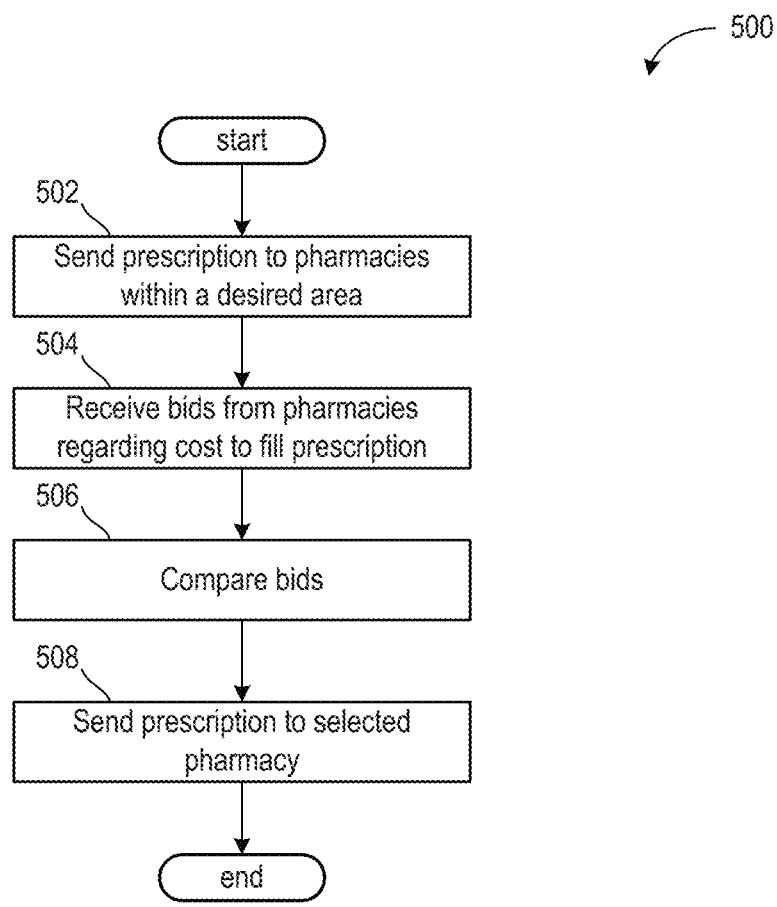
FIG. 7 illustrates an example method for comparing prices, times, and availability of a prescription at two or more pharmacies.

Turning now to FIG. 7, it shows a method 500 for comparing prices at a plurality of pharmacies for a prescription. The method 500 may include sending the prescription prescribed to the patient to a plurality of pharmacies, wherein each pharmacy of the plurality of pharmacies may respond with one or more of a bid, availability, wait time, and distance. Results of the bids and other information provided by the pharmacies may be displayed on the profile associated with the patient, wherein the patient may select a pharmacy of the plurality to fill the prescription.

The method 500 begins at 502, which includes sending the prescription to a plurality of desired pharmacies, as indicated by the patient. The desired pharmacies may meet one or more parameters indicated by the patient, which may include being within a desired area, business hours being within a desired range, availability, in-network for the patient's insurance, and the like. The desired area may be based on a desired radius set by the patient. For example, the patient may set a radius of 10 miles from an initial location (e.g., home, work, prescriber office, etc.), wherein the central server may gather a list of pharmacies within the indicated radius. It will be appreciated that the desired area may be shapes other than circular, for example, the desired area may be square, triangular, or may be a polygon. Additionally or alternatively, the patient may draw a desired area such that the desired area does not resemble a known shape.

The method 500 may proceed to 504, which may include receiving bids from the pharmacies within the desired area. The bids may include one or more of a price, including co-pay, amount covered by insurance, estimated time needed to fill prescription, wait, and the like. Wait may include a number of customers at the pharmacy, wherein as the number of customers increases, the wait may increase. In one example, if the number of customers is relatively high, then the patient may wait in line for more than a desired amount of time to receive their prescription. As such, a pharmacy with a lower wait time may be more desired by some patients.

The method 500 may proceed to 506, which may include comparing the bids received from the pharmacies. The central server may update the patient profile with the pharmacy bids such that the patient may visually compare each of the pharmacies. Additionally or alternatively, the controller may determine averages for each of the data provided by the pharmacies (e.g., cost, distance, etc.) and display the information to the patient profile. Pharmacies may be arranged in correspondence with the average. For example, pharmacies with a cost less than an average cost may be grouped together and pharmacies with a cost greater than the average cost may be grouped together. Additionally or alternatively, an average cost may be based on historical data gathered from previous fillings of the same prescription. The historical data may be provided via other patients and/or via the pharmacies such that the previous fillings may have been executed by other patients as well. This may allow the patient to compare the bids to previous costs of filling the prescription, which may allow the patient to decide to broaden their desired area to include more pharmacies to determine if a lower price is available.

The method 500 may proceed to 508, which may include sending the prescription to the selected pharmacy. The patient may select the pharmacy for a variety of reasons, including one or more of cost, convenience, and availability. At any rate, the central server may inform the pharmacy of the request, wherein the pharmacy may begin preparing the prescription once the request is received.

Figure 8:
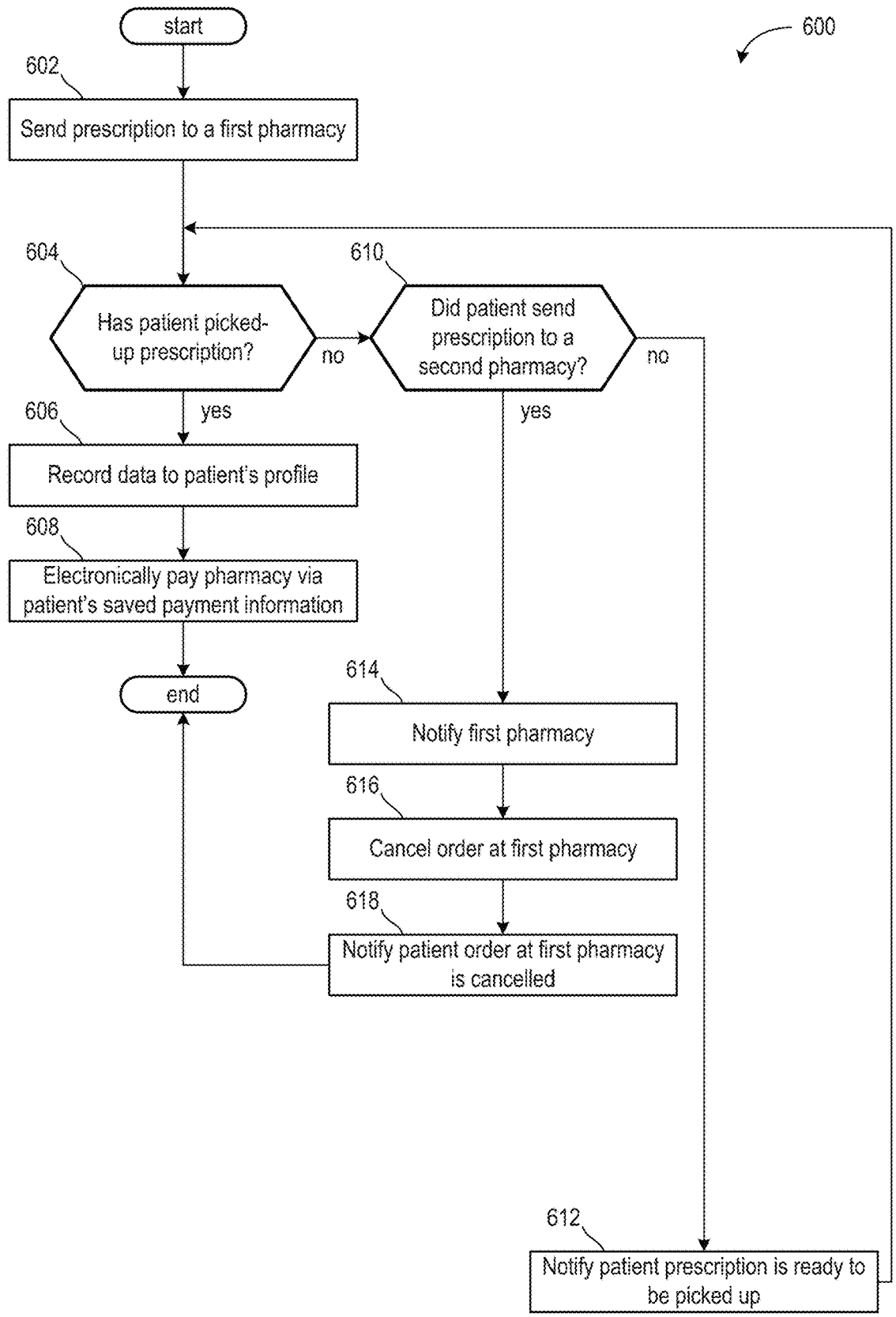
FIG. 8 illustrates an example method monitoring a status of a prescription, wherein the status includes if the prescription has been filled and/or if a location to fill the prescription has been changed.

Turning now to FIG. 8, it shows a method 600 for filling a prescription, paying for a prescription, and recording the prescription being filled to a patient profile. The method may include, in some examples, where the patient's schedule has changed following selecting a pharmacy to fill their prescription, wherein the patient may request to have their prescription filled at a different pharmacy than the pharmacy originally selected. For example, the patient may have selected a first pharmacy based on cost, but then selected the second pharmacy based on convenience (e.g., distance between a current location of the patient and the second pharmacy is less than distance between the current location and the first pharmacy). Additional reasons for changing may include a wait time change, price change, or the like.

The method 600 begins at 602, which may include sending the prescription to a first pharmacy. The prescription, and the request to fill it, along with pertinent patient data, including but not limited to age, prescriber, and insurer, may be sent to the first pharmacy via the central server.

The method 600 may proceed to 604, which may include determining if the patient has picked up their prescription. Determining if the patient has picked up their prescription may include monitoring if the pharmacy has requested payment from the patient.

If the patient has picked up their prescription, then the method 600 may proceed to 606 which may include recording the data to the patient's profile. Recording the patient's data may include the pharmacy sending data regarding time the prescription was picked up, cost, amount of the prescription filled, and the like. In some examples, a pharmacy may be able to fill only a portion of the prescription and in such an example, the pharmacy may relay to the central server that only a portion of the prescription was filled. As such, the patient's prescription may be automatically updated, without instruction from the prescriber, to advance a refill of the patient's prescription based on the portion filled. As an example, if the dosage of the prescription originally demanded a 1-month duration between refills, but the pharmacy was only able to fill half the prescription, then the refill may be advanced to a two-week duration between the half-filled refill and a subsequent refill.

The method 600 may proceed to 608, which may include paying for the prescription electronically via payment information saved to the patient's profile. The payment information may include insurance information, credit card information, debit card information, bank information, and the like. In this way, the patient may receive the prescription at the pharmacy without paying for the prescription at the pharmacy. Additionally or alternatively, the patient may elect, via settings adjusted in their profile, to pay for a co-pay and other portions of the prescription, physically, at the pharmacy. Thus, in some examples, a portion of the prescription may be paid physically and a portion may be paid electronically. Physically paying may differ from electronic payment in that physical payment may include the patient paying with cash, check, credit and/or debit card, and/or the like in-person at the pharmacy, whereas electronic payment may be automatic in response to a request from the pharmacy and may not demand the patient to provide a physical form of payment.

In some examples, additionally or alternatively, the patient may pay for the prescription in-person at the pharmacy during pick-up. The payment may be updated to the patient profile at 606, wherein the updating may include uploading a receipt or the like to the patient profile. As such, 608 may be omitted from the method 600 in the example where the patient pays in-person for the prescription or during another example where a patient has not provided payment information to their profile. In such an example, the pharmacy may be notified by the central server that the patient will be paying physically. The pharmacy may be notified once the prescription is received or in response to the pharmacy relaying to the central server that the prescription is ready for pick-up.

Returning to 604, if the patient has not picked up their prescription, then the method 600 may proceed to 610 to determine if the patient sent the prescription to a second pharmacy. In some examples, the patient's schedule may change, wherein a second pharmacy may be more convenient than the first pharmacy. Convenience may correspond to a distance between the patient and a pharmacy, wherein convenience may increase as the distance decreases. Additionally or alternatively, the second pharmacy may be less expensive and/or may be able to completely fill the patient's prescription whereas the first pharmacy may only be able to partially fill the prescription based on availability.

If a second pharmacy was not selected, then the method 600 may proceed to 612, which may include notifying the patient their prescription is ready to be picked up. In some examples, the prescription may be maintained ready for pick-up at the pharmacy for a threshold duration. The threshold duration may be greater than 24 hours and less than a month. In some examples, the threshold duration is between 3-7 days. Once the threshold duration has elapsed, the patient may be notified of the expiration and commanded to select a new pharmacy.

If a second pharmacy was selected, then the method 600 may proceed to 614 to notify the first pharmacy. The first pharmacy may restock the prescription such that the patient may no longer purchase the prescription at the first pharmacy. This may prevent and/or mitigate fraud.

The method 600 may proceed to 616, which may include cancelling the order at the first pharmacy. The method 600 may proceed to 618, which may include notifying the patient that order at the first pharmacy has been cancelled. As such, the patient may no longer receive the prescription at the first pharmacy and may only receive the prescription from the second pharmacy.

In some examples, the prescription may be available at both the first and second pharmacies, wherein once the patient purchases the prescription at the first pharmacy or the second pharmacy then the prescription may no longer be available at the other pharmacy. In this way, the prescription may be available at more than one pharmacy, but the method may prevent the patient from purchasing the prescription more than once.

Figure 9:
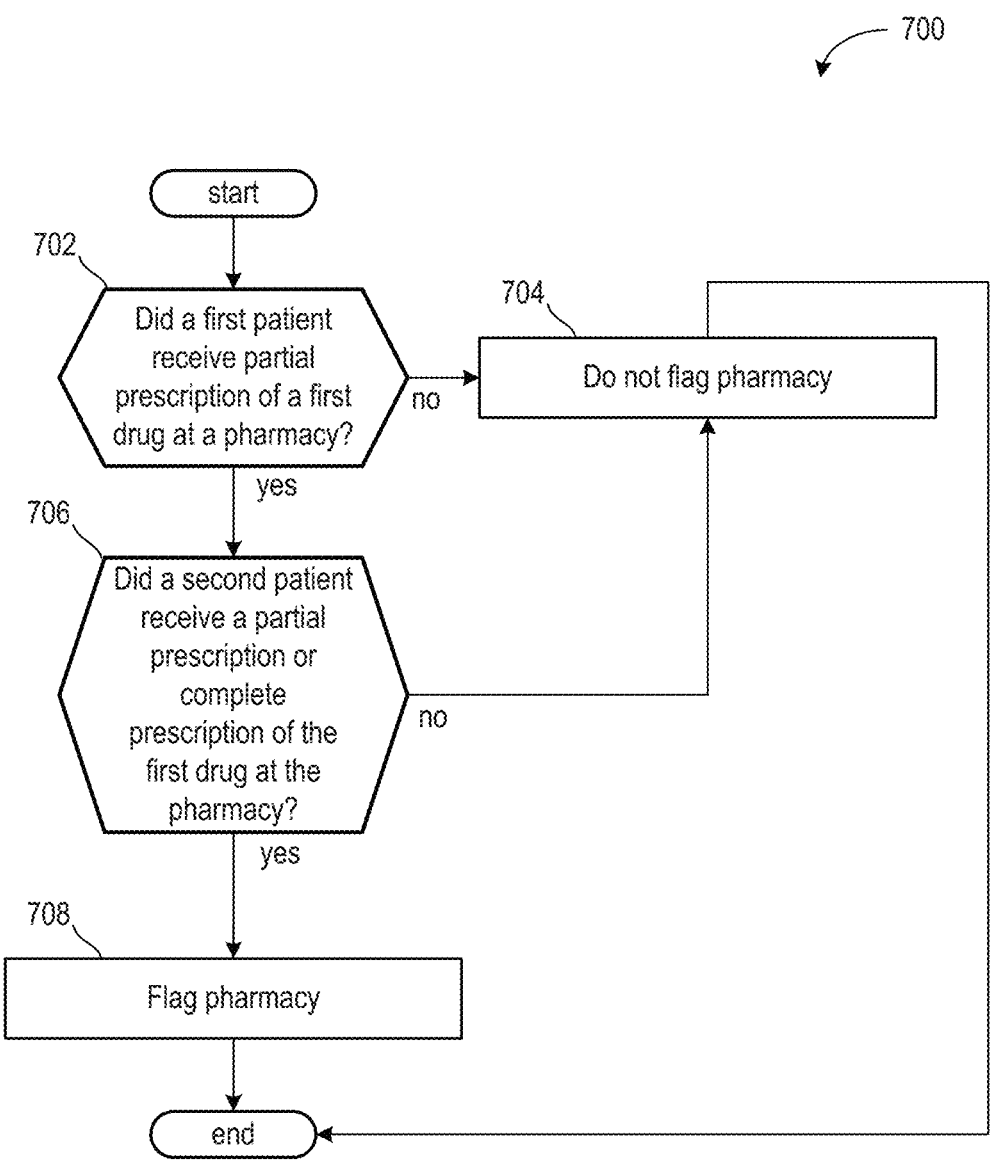
FIG. 9 illustrates an example method for determining fraud.

Turning now to FIG. 9, it shows a method 700 for determining pharmaceutical fraud. For example, a patient may pay a copay upon receiving a prescription, wherein the copay may be fixed regardless of a dosage of the prescription. Thus, the copay may be the same if the prescription is partially filled or completely filled. In this way, the method 700 may be a method for detecting fraud committed by a pharmacy, wherein the pharmacy may partially fill multiple prescriptions of the same drug, thereby allowing the pharmacy to receive increased pay due to the increased number of copays.

The method 700 begins at 702, which includes determining if a first patient receive a partial prescription of a first drug at a pharmacy. The partial prescription may be defined as comprising a portion and/or a percentage of a complete prescription. For example, if the complete prescription is detailed to comprise a number of doses corresponding to X number of days, then the partial prescription may comprise a number of doses corresponding to less than X number of days. In one example, if the complete prescription is for 30 days, then the partial prescription may be for less than 30 days. If the first patient received a complete prescription and did not receive the partial prescription, then the method 700 may proceed to 704, which may include not flagging the pharmacy. As such, the pharmacy may not be committing fraud.

If the first patient received only the partial prescription of the first drug at the pharmacy, then the method 700 may proceed to 706, which may include determining if a second patient received a partial prescription or a complete prescription of the first drug at the pharmacy. If the second patient did not receive the partial prescription or the complete prescription of the first drug, then the method 700 may proceed to 704, which may include not flagging the pharmacy. In this way, the second patient may not have any of the first drug following the partial prescription of the first patient, which may indicate that the first patient received an entire inventory of the first drug from the first pharmacy. By doing this, the pharmacy may be out of stock of the first drug and may have depleted their stock of the first drug by partially filling the prescription of the first patient.

If the second patient received the partial prescription or the complete prescription of the first drug, then the method 700 may proceed to 708 to flag the pharmacy. In this way, the pharmacy may be attempting to increase a number of copays received by partially filling some prescriptions of the first drug. That is to say, the pharmacy may comprise a sufficient amount of the first drug to completely fill the prescription of the first patient, however, the pharmacy selected to partially fill the prescription of the first drug to allow the pharmacy to at least partially fill another prescription of the first drug, thereby allowing the pharmacy to receive an extra copay. By flagging the pharmacy, a behavior of the pharmacy may be tracked over time to determine if partially filling patient prescriptions is repeated.

In some examples, the pharmacy may only partially fill the prescription due to a lack of inventory, however, a shipment of the first drug may occur following partially filling the prescription, wherein the pharmacy may by happenstance be able to completely fill a prescription of the first drug subsequent partially filling the prescription of the first drug. In this way, the pharmacy may not be committing fraud.

FIG. 10 shows an example user interface 1200 that may be presented to a patient via a patient device (e.g., via a display of patient device 160 of FIG. 1 and/or patient device 202 of FIG. 2). The user interface 1200 may be presented upon the patient selecting a particular prescription (that is eligible to be filled or refilled) from an electronic prescription wallet associated with the patient. The user interface 1200 may include prescription details 1202, which may include information such as an identifier of the medication associated with the prescription (e.g., a type, brand, size/concentration, etc.), a quantity and form (e.g., liquid, pill, tablet, powder, etc.) of the medication, directions/dosage information for the medication, prescriber information (e.g., indicating a prescriber that directed the generation of the prescription), date of prescription, number of fills/refills available for the prescription (e.g., including an expiration of the prescription), number of previous fills/refills of the prescription, image of the medication, and/or other information.

The user interface 1200 may further include shopping information 1204, which may provide a user-friendly mechanism for assisting a user in selecting a pharmacy for filling the prescription. The shopping information 1204 may include a map of pharmacies (e.g., in a region selected based on patient preferences and/or a current location of a patient) that may be used to fill the prescription. The map of pharmacies may be interactive, allowing the patient to provide input to change the map parameters (e.g., zoom, pan, etc.) and/or to select pharmacies displayed on the map to receive information regarding the selected pharmacies. In some examples, the shopping information 1204 may include an indication of one or more pharmacies at which one or more recent prescriptions have been filled or refilled by the patient. For example, if the patient is shopping for a refill of an electronic prescription, the shopping information 1204 may highlight (e.g., by providing a textual indication or a graphical indication, such as by changing a color of an indicator on the interactive map) or otherwise indicate a pharmacy at which an initial fill or prior refill of the electronic prescription was completed. In this way, the patient may quickly select whether to use the same pharmacy for the current refill or to use a different pharmacy (e.g., if the service or cost of the prior pharmacy was not satisfactory), thereby maintaining control of the filling process of the electronic prescription.

The shopping information 1204 may also include information blocks 1206 for one or more pharmacies (e.g., a subset of the pharmacies shown in the map). The information blocks 1206 may identify selected pharmacies and provide address information (e.g., including a distance from a current or saved location of the patient), operating hours, estimated wait time (e.g., based on real-time monitoring and/or historical indications of wait time for that pharmacy), contact information, and a patient-specific cost for filling the prescription (e.g., the prescription identified in the prescription details 1202) at that pharmacy. The information blocks 1206 may also include a selectable user interface element that is selectable to control the patient device to request the prescription to be sent (e.g., from the central service/electronic prescription wallet) to the associated pharmacy for filling. The number of information blocks 1206 shown in the user interface 1200 may be determined by user preferences, prescription cost results, number of pharmacies available to fill the prescription, display size for display showing the user interface 1200, and/or other parameters. The pharmacies selected for presentation via the information blocks 1206 may also be determined by one or more of the above criteria (e.g., user preferences, prescription cost results, etc.). In some examples, the information blocks 1206 may represent the pharmacies that provided the lowest cost for filling the prescription (e.g., of the pharmacies that fit the preferences of the patient). The information blocks 1206 may additionally or alternatively include prior pharmacies that the patient has used for prior fills of the electronic prescription (or for a different electronic prescription), even if the cost or location of the prior pharmacies is not the lowest/closest (respectively). In some examples, one or more pharmacies that do not fit the preferences of the patient but that provided a lower cost for filling the prescription than pharmacies that do fit the preferences of the patient may be shown in order to provide the patient the opportunity to select a cheapest option for filling the prescription. In such examples, an indication of how the pharmacy does not fit the preferences (e.g., located outside a preferred zone, operates outside preferred business hours, not part of a preferred chain(s)/store type, etc.) may be included in the information block to aid the user in making a decision regarding selection of the pharmacy for filling the prescription. The cost information for filling the prescription may be automatically acquired by the central service (e.g., continuously updated and/or requested responsive to the user selecting the prescription and/or requesting the system to shop the prescription at different pharmacies) to determine the suggested pharmacies indicated by the information blocks 1206.

In this way, a third party system may receive a prescription from a prescriber, wherein the third party system may allow a patient to maintain control of the prescription for a total duration of the prescription. The third party system may allow the patient to change pharmacies for a present filling of the prescription or for future fillings of the prescription without directly contacting a pharmacy. The third party system may further allow the patient to compare bids for filling the prescription and pay for the prescription via payment information saved to a profile of the patient. The technical effect of the third party system is to allow the patient to more easily control their prescription, while saving each of the patient, prescriber, and pharmacy time.

FIG. 11 illustrates example approaches for securing transmissions of data relating to managing prescriptions. Approach A in FIG. 11 represents a non-networked prescription filling/refilling mechanism 1102, in which each pharmacy 1104a, 1104b, and 1104c stores and/or passes data for each prescription that is received at the respective pharmacy. In the mechanism 1102, a first pharmacy selected to fill a prescription may store all information of the prescription (e.g., as opposed to storing a single instance of the prescription, as described in examples above). If a patient desires to transfer the prescription to be filled at a second, different pharmacy, the patient may request the first pharmacy to transfer the prescription out to the second pharmacy. Accordingly, the data for the prescription may be transmitted from the first pharmacy to the second pharmacy. All or a portion of the data for the prescription may be stored at the first pharmacy even after transmission of the prescription to the second pharmacy (e.g., the transmission may correspond to a copy of the prescription information). Accordingly, each time a patient transfers the prescription, the number of pharmacies storing data relating to the prescription may increase.

Approach B in FIG. 11 represents a secured, networked prescription filling/refilling mechanism 1306, in which a central system 1308 may manage the transmission of data relating to a prescription of a patient utilizing blockchain technology (and/or another data security mechanism) to secure the transmission of data between different devices. A blockchain may be used to allow the data relating to prescriptions (e.g., data sent between consumer devices, central devices, and/or pharmacies) to be distributed, but not copied, thereby creating a digital ledger that records prescription transactions in a secure manner that resists corruption/unauthorized tampering with the data while simultaneously allowing access to the data for authorized parties (e.g., such that an entity is not "locked out" of viewing or managing the data while another entity is viewing or managing the data). In this way, data regarding a prescription for a patient may be provided to a pharmacy for filling/refilling the prescription, without taking control of the prescription away from the patient. A blockchain is formed of a list of records/blocks that are linked using cryptography. Each block includes a cryptographic hash of the previous block, a timestamp, and transaction data (e.g., data related to an electronic prescription).

The central system 1308 may include and/or correspond to the electronic prescription wallet central server 120 of FIG. 1, the central service 208 of FIG. 2, the electronic wallet 1002 of FIG. 3/1102 of FIG. 4, and/or any other suitable computing system. The central system 1308 may be in communication with one or more pharmacies, such as pharmacy 1310, and one or more consumer or patient devices, such as consumer device 1312. The consumer device 1312 may include a consumer interface configured to enable a consumer (e.g., a patient) to interactively manage prescriptions associated with the consumer. For example, the consumer interface may include a graphical user interface or other interfacing element with which the consumer may interact to request a prescription fill or refill. In an example execution of a prescription refilling method, a request for a prescription refill made at the consumer device 1312 (e.g., via the consumer interface) may be transmitted to the central system 1308.

Transmissions between devices/systems in Approach B may be secured using public and private keys. A public key (e.g., a long, randomly-generated string of numbers) may correspond to an address for a user on a blockchain. Prescription data for the user/patient that is sent across a network may be recorded as belonging to that address. A private key may be similar to a password and may be used to provide a user/patient with access to electronic prescriptions (e.g., prescriptions in the patient's wallet, as described above with respect to FIGS. 1-4). The consumer device may store a patient private key, which may be used to decrypt data that is encrypted using an associated public key, such as a refill public key. The central system 1308 may utilize the patient private key (which may be stored in association with the corresponding patient) to decrypt data as described above, and the central system 1308 may further store a refill public key to encrypt prescription data. For example, responsive to receiving the refill request from the consumer device, the central system 1308 may encrypt a request for prescription refill availability information using the refill public key. Information regarding the prescription refill (e.g., transaction data regarding a number of times the prescription has been filled) may be maintained in a blockchain 1314. Accordingly, the central system 1308 may send a request (e.g., encrypted using the refill public key) for a prescription refill availability (e.g., requesting whether the prescription has a refill that has not yet been filled) to the blockchain 1314. Sending the request to the blockchain 1314 may include accessing the records stored in the blockchain 1314 to determine the transaction history associated with the prescription (e.g., the number of times the prescription has been filled versus the number of refills allotted for the prescription). An indication of whether a refill is available may be determined using the information in the blockchain 1314.

Responsive to determining that a refill is available for the prescription, the central system may transmit a refill request to the pharmacy 1310 for refilling the prescription. The pharmacy 1310 may transmit an indication to the central system 1308 that the prescription was filled once the prescription refill is picked up by the patient and/or delivered to the patient. In response to the indication that the prescription refill has been filled, the central system 1308 may update the blockchain 1314 to record the prescription refill (e.g., to decrease the available refills for the prescription by one).

In this way, the transactions regarding the prescription may be easily auditable, while still allowing the sensitive patient data relating to the patient to be maintained by the patient and secured to prevent tampering/snooping. The blockchain approach described above may increase security while decreasing delays associated with accessing and modifying data regarding prescription fills/refills.

In one embodiment, a method for tracking execution of a prescription prescribed by a prescriber, the method comprises receiving, at a central service, an electronic prescription from a prescriber device for a patient, correlating, with a processor of the central service, the electronic prescription to a patient wallet associated with the patient and storing the electronic prescription in association with the patient wallet, the patient wallet being stored in an electronic prescription wallet database, generating, with the processor, a prescription fill request including a single instance of the electronic prescription, transmitting, via a communication interface of the central service, the prescription fill request to a pharmacy system, and updating, with the processor, the patient wallet to indicate the transmission of the prescription fill request to the pharmacy system.

A first example of the method further comprises transmitting, via the communication interface, a payment for the electronic prescription according to payment information associated with the patient wallet in response to receiving a receipt from the pharmacy system, and updating the patient wallet to include a receipt from the pharmacy system, the receipt including one or more of a cost, a dose, and a location of a pharmacy associated with the pharmacy system.

A second example of the method, optionally including the first example, further includes where the pharmacy is a first pharmacy of a plurality of pharmacies or a centralized data service associated with the plurality of pharmacies, wherein the method further comprises sending a request for a bid or cost estimate to fill the prescription to a plurality of pharmacies or the centralized data service, receiving a plurality of bids or cost estimates from the plurality of pharmacies or the centralized data service, and updating the patient wallet to associate the plurality of bids or cost estimates to the electronic prescription and the plurality of pharmacies.

A third example of the method, optionally including any of the previous examples, further includes where the pharmacy system is selected based on one or more settings stored in the database and associated with the patient profile and/or based on user input from a patient to which the prescription is prescribed.

A fourth example of the method, optionally including any of the previous examples, further includes where the prescription fill request includes a subset of data from the electronic prescription.

An embodiment of a patient-directed electronic prescription management system comprises a central server including a processor and non-transitory memory, the central server being in communication with an electronic prescription wallet database, the non-transitory memory storing instructions executable by the processor to receive a prescription for a patient from a prescriber device, update a patient wallet to include a dose and a drug corresponding to the prescription, where the patient wallet is associated with the patient and stored in the electronic prescription wallet database, transmit a cost estimate request corresponding to the prescription to respective pharmacy systems associated with a plurality of pharmacies and/or transmit the cost estimate request to a centralized data service, receive bids or cost estimates from the respective pharmacy systems and/or the centralized data service, update the patient wallet to include the bids or cost estimates, and transmit an indication of the bids or cost estimates to a patient device for display.

A first example of the system further includes where the instructions are further executable to receive a request from the patient to compare cost estimates associated with filling the prescription at each of the plurality of pharmacies.

A second example of the system, optionally includes the first example, further includes where the cost estimate request is transmitted to the respective pharmacy systems and/or the centralized data service automatically without a request from the patient.

A third example of the system, optionally includes any of the previous examples, further includes where the instructions are further executable to receive a request to fill the prescription at a selected pharmacy associated with one of the plurality of pharmacy systems and/or the centralized database, generate and transmit a single instance representing the prescription to the respective pharmacy system and/or centralized database associated with the selected pharmacy, and transmit payment information to the respective pharmacy system in response to receiving a receipt from the respective pharmacy system indicating the prescription has been picked up or is being delivered to the patient.

A fourth example of the system, optionally includes any of the previous examples, further includes where the receipt is saved to the patient wallet, and where the processor correlates the prescription filled at the pharmacy with the prescription associated in the patient wallet, wherein the correlating includes automatically updated the prescription to decrease the dose of the prescription based on an amount of the prescription filled by the pharmacy.

A fifth example of the system, optionally includes any of the previous examples, further includes where the plurality of pharmacies are selected based on one or more preferences associated with the patient wallet, the one or more preferences including an area, a cost, a wait time, an availability, and hours of operation associated with the plurality of pharmacies.

A sixth example of the system, optionally includes any of the previous examples, further includes where the central server receives the prescription responsive to receiving and validating authenticating data from the prescriber device including a username, a password, and a prescriber identification number.

A seventh example of the system, optionally includes any of the previous examples, further includes where the central server transmits the indication of the bids or cost estimates responsive to receiving and validating authenticating data from the patient device, wherein validating the authenticating data from the patient data comprises the processor correlating the authenticating data from the patient device to the patient wallet, and wherein the authenticating data from the patient device is different than the authenticating data from the prescriber device, and wherein the pharmacy is a first pharmacy and wherein the instructions are further executable to receive a request to refill the prescription at a second pharmacy different than the first pharmacy, and wherein the instructions are further executable to compare data associated with a plurality of patient wallets, wherein the data includes prescription amount, pharmacy location, prescription cost, and wait time.

An embodiment of a method comprises receiving an electronic prescription at a central server, the electronic prescription received from a prescriber device via a network, correlating the electronic prescription via a processor of the central server to a patient wallet stored in a database, wherein the correlating includes comparing a patient identification received with the electronic prescription to a patient identification stored in the database, generating, via the processor, a first single instance of the electronic prescription, the first single instance of the electronic prescription including a first of a plurality of fills for the electronic prescription, transmitting, via a communication interface of the central server, the first single instance of the electronic prescription to a first pharmacy system, updating the electronic prescription in the patient wallet to indicate a transmission of the first fill for the electronic prescription, after the first single instance of the electronic prescription is filled and responsive to a patient request for a refill of the electronic prescription, generating, via the processor, a second single instance of the electronic prescription, the second single instance of the electronic prescription including a second of the plurality of fills for the electronic prescription, transmitting, via the communication interface, the second single instance of the electronic prescription to a second pharmacy system, and updating the electronic prescription in the patient wallet to indicate a transmission of the second fill of the electronic prescription.

A first example of the method further includes where receiving a receipt from the first pharmacy system, the receipt indicating the first fill of the electronic prescription is picked up by the patient or is being delivered to the patient.

A second example of the method, optionally including the first example, further includes where sending payment information in response to receiving the receipt, wherein the payment information includes one or more of health insurance information, credit card information, debit card information, and bank information.

A third example of the method, optionally including any of the previous examples, further includes where updating the electronic prescription in the patient wallet based on receiving the receipt, the receipt indicating an amount of prescription received by the patient from the pharmacy, wherein receiving the electronic prescription further comprises receiving authenticating credentials from a prescriber associated with the prescriber device, the authenticating credentials comprising a username, a password, and an identification number.

A fourth example of the method, optionally including any of the previous examples, further includes where a second pharmacy associated with the second pharmacy system is located in a different state than a first pharmacy associated with the first pharmacy system.

A fifth example of the method, optionally including any of the previous examples, further includes where the first pharmacy system and the second pharmacy system are selected based on preferences stored in the database, the preferences including one or more of a proximity of pharmacies associated with the patient and a cost of filling the electronic prescription.

A sixth example of the method, optionally including any of the previous examples, further includes where responsive to the first single instance of the prescription being filled, sending an indication of the fill to a blockchain to update a record associated with the prescription, further comprising, responsive to the patient request for the refill, accessing a record of the prescription in a blockchain to determine a number of refills available for the prescription, and only generating the second single instance of the prescription responsive to determining that the number of refills available for the prescription is greater than zero.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for tracking execution of a prescription prescribed by a prescriber, the method comprising:
   receiving, at a central server, an electronic prescription from a prescriber device for a patient inputted by a prescriber, wherein a controller of the central server correlates authenticating data to a prescriber profile stored in an electronic prescription wallet database;
   looking-up, with the central server, regional rules in a rules database that comprises a plurality of prescription rules, the regional rules associated with one or more of a residence of the patient and/or a location of the prescriber, and each prescription rule may include data indicating the particular laws and/or regulations for electronic prescribing for a particular geographic region in a format that may be read by the controller so that one or more operations based on the retrieved prescription rule(s) for a particular geographic region are performed;
   correlating, with the controller of the central server, the electronic prescription to a patient wallet associated with the patient and storing the electronic prescription in association with the patient wallet, the patient wallet being stored in the electronic prescription wallet database;
   generating, with the controller and based on computer-readable instructions stored on memory thereof, a prescription fill request, sent from a patient device via the patient to the prescriber device, including a single instance of the electronic prescription correlated to a patient profile associated with the patient wallet and stored in the electronic prescription wallet database, the correlation including matching patient data transmitted with the electronic prescription to data stored in a patient database of the electronic prescription wallet database;
   transmitting, via a communication interface of the central server, the prescription fill request to a pharmacy system and a blockchain, wherein the central server employs one or more suitable communication protocols defining rules and data formats for exchanging information and communicating over a network between the central server, the prescriber device, the patient device, and the pharmacy system;
   automatically sending a request for a bid or a cost estimate to fill the prescription to a plurality of pharmacies or a centralized data service based on inputs provided to the patient device by the patient in a format understandable to the patient in response to information stored on the blockchain indicating a refill is available for the electronic prescription, wherein the bid and the cost estimate are correlated to the patient profile;
   receiving a plurality of bids or cost estimates from the plurality of pharmacies or the centralized data service and adjusting a display of the patient profile;
   prioritizing search preferences for finding the plurality of pharmacies in a pharmacy database based on prices, proximity to the patient, availability of the prescription, and wait times at the plurality of pharmacies;
   updating, with the controller, the patient wallet to indicate the transmission of the prescription fill request to the pharmacy system and to associate the plurality of bids or cost estimates to the electronic prescription and the plurality of pharmacies;
   cancelling the prescription at a pharmacy and sending the prescription to a different pharmacy based on an input provided by the patient via the patient device, wherein the patient device sends a request to access the patient profile to change the pharmacy for filling the prescription;
   sending a receipt from the pharmacy system to the central server in response to the prescription being filled and ready for pick-up at a pharmacy of the plurality of pharmacies, wherein the prescription is filled in response to the patient selecting the pharmacy via inputs provided to the patient device;
   creating a digital ledger that records prescription transactions on the blockchain, wherein prescription transactions include data related to the prescription fill request, the receipt, a transaction history associated with the prescription, and each block includes a cryptographic hash of the previous block, a timestamp, and transaction data; and
   automatically indicating the refill is unavailable to the patient via a display of the patient device based on information stored on the blockchain.

2. The method of claim 1, further comprising transmitting, via the communication interface, a payment for the electronic prescription according to payment information associated with the patient wallet in response to receiving the receipt from the pharmacy system, and updating the patient wallet to include the receipt from the pharmacy system, the receipt including one or more of a cost, a dose, and a location of a pharmacy associated with the pharmacy system.

3. The method of claim 1, wherein the patient device and/or the prescriber device is one or more of a personal/desktop computer, a portable computer, and a mobile device.

4. The method of claim 1, wherein the pharmacy system is selected based on one or more settings stored in the electronic prescription wallet database and associated with the patient profile and/or based on user input from a patient to which the prescription is prescribed.

5. The method of claim 1, wherein the prescription fill request includes a subset of data from the electronic prescription.

6. A patient-directed electronic prescription management system, comprising:
   a central server including a controller and non-transitory memory, the central server being in communication with an electronic prescription wallet database, the non-transitory memory storing instructions executable by the controller to:

receive, at the central server, a prescription for a patient from a prescriber device inputted by a prescriber, wherein the controller of the central server correlates authenticating data to a prescriber profile, associated with the prescriber, stored in the electronic prescription wallet database;

look-up, with the central server, regional rules in a rules database that comprises a plurality of prescription rules, the regional rules associated with one or more of a residence of the patient and/or a location of the prescriber, and each prescription rule may include data indicating the particular laws and/or regulations for electronic prescribing for a particular geographic region in a format that may be read by the controller so that one or more operations based on the retrieved prescription rule(s) for a particular geographic region are performed;

update a patient wallet and a blockchain to include a dose and a drug corresponding to the prescription, where the patient wallet is associated with the patient and stored in the electronic prescription wallet database;

receive a request from the patient via inputs provided to a patient device in a format understandable to the patient to compare cost estimates associated with filling the prescription at each of a plurality of pharmacies in response to a refill of the prescription being available based on information stored on the blockchain;

prioritize search preferences for finding the plurality of pharmacies in a pharmacy database based on prices, proximity to the patient, availability of the prescription, and wait times at the plurality of pharmacies;

transmit a cost estimate request corresponding to the prescription to respective pharmacy systems associated with the plurality of pharmacies and/or transmit the cost estimate request to a centralized data service, wherein the patient device transmits the cost estimate based on inputs provided by the patient to the patient device in a format understandable to the patient;

receive bids or cost estimates from the respective pharmacy systems and/or the centralized data service, wherein the bid or cost estimates are correlated to the patient profile;

update the patient wallet to include the bids or cost estimates via adjusting a display of the patient profile;

transmit an indication of the bids or cost estimates to the patient device for display;

receive a request to fill the prescription at a selected pharmacy associated with one of the plurality of pharmacies and/or the centralized database, and generate and transmit a single instance representing the prescription to the respective pharmacy system and/or centralized database associated with the selected pharmacy, the prescription correlated to the patient profile associated with the patient wallet and stored in the electronic prescription wallet database, the correlation including matching patient data transmitted with the electronic prescription to data stored in the patient database of the electronic prescription wallet database;

cancel the prescription at the selected pharmacy and send the prescription to a different pharmacy based on an input provided by the patient via the patient device, wherein the patient device sends a request to access the patient profile to change a pharmacy for filling the prescription;

transmit payment information to the different pharmacy in response to receiving a receipt from the different pharmacy indicating the prescription has been picked up or is being delivered to the patient, wherein the different pharmacy is selected by the patient via inputs provided to the patient device;

create a digital ledger that records prescription transactions in the blockchain, each block including a cryptographic hash of the previous block, a timestamp, and transaction data, wherein the central server employs one or more suitable communication protocols defining rules and data formats for exchanging information and communicating over a network between the central server, the prescriber device, the patient device, and the pharmacy system; and automatically indicate the refill of the prescription is unavailable on a display of the patient device based on information stored on the blockchain.

7. The system of claim 6, wherein the receipt is saved to the patient wallet, and where the controller correlates the prescription filled at the pharmacy with the prescription associated in the patient wallet, and wherein the correlating includes automatically updating the prescription to decrease the dose of the prescription based on an amount of the prescription filled by the pharmacy.

8. The system of claim 6, wherein the plurality of pharmacies are selected based on one or more preferences associated with the patient wallet, the one or more preferences including an area, a cost, a wait time, an availability, and hours of operation associated with the plurality of pharmacies.

9. The system of claim 6, wherein the central server receives the electronic prescription responsive to receiving and validating authenticating data from the prescriber device including a username, a password, and a prescriber identification number.

10. The system of claim 9, wherein the central server transmits the indication of the bids or cost estimates responsive to receiving and validating authenticating data from the patient device, wherein validating the authenticating data from the patient data comprises the controller correlating the authenticating data from the patient device to the patient wallet, wherein the authenticating data from the patient device is different than the authenticating data from the prescriber device, wherein the instructions are further executable to compare data associated with a plurality of patient wallets, and wherein the data includes prescription amount, pharmacy location, prescription cost, and wait time.

11. A method for tracking execution of a prescription prescribed by a prescriber, the method comprising:

receiving an electronic prescription at a central server, the electronic prescription received from a prescriber device via a network based on inputs provided by the prescriber to the prescriber device, wherein a controller of the central server correlates authenticating data to a prescriber profile stored in an electronic prescription wallet database;

looking-up, with the central server, regional rules in a rules database that comprises a plurality of prescription rules, the regional rules associated with one or more of a residence of the patient and/or a location of the prescriber, and each prescription rule may include data indicating the particular laws and/or regulations for electronic prescribing for a particular geographic region in a format that may be read by the controller so that one or more operations based on the retrieved prescription rule(s) for a particular geographic region are performed;

correlating the electronic prescription via the controller of the central server to a patient wallet stored in the electronic prescription wallet database based on a prescription request sent from a patient device to the prescriber device, the patient requesting the prescription based on inputs provided to the patient device, wherein the correlating includes comparing a patient identification received with the electronic prescription to a patient identification stored in the electronic prescription wallet database;

prioritizing search preferences for finding a plurality of pharmacies in a pharmacy database based on prices, proximity to the patient, availability of the prescription, and wait times at the plurality of pharmacies;

sending a request for a bid or a cost estimate to fill the prescription to the plurality of pharmacies or a centralized data service;

receiving a plurality of bids or cost estimates from the plurality of pharmacies or the centralized data service and adjusting a display of a patient profile;

generating, via the processor, a first single instance of the electronic prescription, the first single instance of the electronic prescription including a first of a plurality of fills for the electronic prescription correlated to the patient profile associated to the patient wallet and stored in the electronic prescription wallet database, the correlation including matching patient data transmitted with the electronic prescription to data stored in the patient database of the electronic prescription wallet database;

transmitting, via a communication interface of the central server, the first single instance of the electronic prescription to a first pharmacy system of a first pharmacy in response to the patient selecting the first pharmacy via inputs provided to the patient device, wherein the central server employs one or more suitable communication protocols defining rules and data formats for exchanging information and communicating over a network between the central server, the prescriber device, the patient device, and the pharmacy system;

updating the electronic prescription in the patient wallet to indicate a transmission of a first fill for the electronic prescription;

cancelling the first fill at the first pharmacy in response to the first single instance of the electronic prescription being sent to a second pharmacy of a second pharmacy system prior to the prescription at the first pharmacy being purchased based on an input provided by the patient via the patient device in a format understandable to the patient, wherein the patient device sends a request to access the patient profile to change a pharmacy for filling the prescription;

after the first single instance of the electronic prescription is filled and picked up by the patient at the second pharmacy or delivered to the patient and responsive to a patient request for a refill of the electronic prescription, generating, via the controller, a second single instance of the electronic prescription, the second single instance of the electronic prescription including a second of the plurality of fills for the electronic prescription;

responsive to the first single instance of the electronic prescription being filled, sending an indication of the fill to a blockchain to update a record associated with the prescription, and further comprising, responsive to the patient request for the refill, accessing a record of the prescription in the blockchain to determine a number of refills available for the prescription, and only generating the second single instance of the electronic prescription responsive to determining that the number of refills available for the prescription is greater than zero;

automatically denying the second single instance of the electronic prescription responsive to the number of refills available for the prescription being equal to zero based on the record of the prescription in the blockchain;

transmitting, via the communication interface, the second single instance of the electronic prescription to a third pharmacy system;

updating the electronic prescription in the patient wallet to indicate a transmission of a second fill of the electronic prescription;

creating a digital ledger that records prescription transactions on the blockchain, wherein prescription transactions include data related to the prescription fill request, the receipt, a transaction history associated with the prescription, and each block includes a cryptographic hash of the previous block, a timestamp, and transaction data; and automatically indicating the refill is unavailable to the patient via a display of the patient device based on information stored on the blockchain.

12. The method of claim 11, further comprising receiving a receipt from the second pharmacy, the receipt indicating the first fill of the electronic prescription is picked up by the patient or is being delivered to the patient.

13. The method of claim 12, further comprising sending payment information in response to receiving the receipt, wherein the payment information includes one or more of health insurance information, credit card information, debit card information, and bank information.

14. The method of claim 13, further comprising updating the electronic prescription in the patient wallet based on receiving the receipt, the receipt indicating an amount of prescription received by the patient from the pharmacy, wherein receiving the electronic prescription further comprises receiving authenticating credentials from a prescriber associated with the prescriber device, the authenticating credentials comprising a username, a password, and an identification number.

15. The method of claim 11, wherein a third pharmacy associated with the third pharmacy system is located in a different state than the first pharmacy associated with the first pharmacy system and the second pharmacy associated with the second pharmacy system.

16. The method of claim 15, wherein the first pharmacy system and the second pharmacy system are selected based on preferences stored in the electronic prescription wallet database, the preferences including one or more of a proximity of pharmacies associated with the patient and a cost of filling the electronic prescription.

* * * * *